(12) United States Patent
Groβ et al.

(10) Patent No.: US 8,765,774 B2
(45) Date of Patent: Jul. 1, 2014

(54) 3-ARYLQUINAZOLIN-4-ONE COMPOUNDS FOR COMBATING INVERTEBRATE PESTS

(75) Inventors: Steffen Groβ, Ludwigshafen (DE); Karsten Körber, Eppelheim (DE); Wolfgang von Deyn, Neustadt (DE); Florian Kaiser, Mannheim (DE); Prashant Deshmukh, Mannheim (DE); Joachim Dickhaut, Heidelberg (DE); Nina Gertrud Bandur, Mannheim (DE); Arun Narine, Mannheim (DE); Matthias Pohlman, Freinsheim (DE); Michael Puhl, Hirschberg (DE); Sarah Thompson, Raleigh, NC (US); Cecille Ebuenga, Laguna (PH); Douglas D. Anspaugh, Apex, NC (US); Deborah L. Culbertson, Fuquay Varina, NC (US); Hassan Oloumi-Sadeghi, Raleigh, NC (US); Faraneh Oloumi, legal representative, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 87 days.

(21) Appl. No.: 13/254,182

(22) PCT Filed: Mar. 3, 2010

(86) PCT No.: PCT/EP2010/052693
§ 371 (c)(1),
(2), (4) Date: Nov. 14, 2011

(87) PCT Pub. No.: WO2010/100189
PCT Pub. Date: Sep. 10, 2010

(65) Prior Publication Data
US 2012/0053052 A1    Mar. 1, 2012

Related U.S. Application Data

(60) Provisional application No. 61/157,375, filed on Mar. 4, 2009.

(51) Int. Cl.
*A01N 43/54*      (2006.01)
*A61K 31/517*     (2006.01)
*C07D 401/00*     (2006.01)
*C07D 403/00*     (2006.01)
*C07D 413/00*     (2006.01)
*C07D 417/00*     (2006.01)
*C07D 419/00*     (2006.01)

(52) U.S. Cl.
USPC ..................... 514/266.21; 544/284

(58) Field of Classification Search
None
See application file for complete search history.

(56) References Cited

U.S. PATENT DOCUMENTS

| | | |
|---|---|---|
| 3,755,581 A | 8/1973 | Janiak |
| 6,509,354 B1 | 1/2003 | Toriyabe et al. |
| 2006/0106042 A1 | 5/2006 | Fischer et al. |

FOREIGN PATENT DOCUMENTS

| | | |
|---|---|---|
| DE | 195 47 475 | 1/1997 |
| EP | 1 076 053 | 2/2001 |

OTHER PUBLICATIONS

International Search Report in International Application No. PCT/EP2010052693, filed Mar. 3, 2010.
International Preliminary Report on Patentability in International Application No. PCT/EP2010/052693, filed Mar. 3, 2010.
Hempel, Andrew, et al., "7,8-dihydroxy-4-propyl-1,2,3,4,4a,5,6,10b-octahydro-benzo[ƒ]quinolinium bromide monohydrate, a dopamine agonist", Acta Cryst, 2005, pp. o681-o682, vol. C61.

*Primary Examiner* — Jeffrey H Murray
(74) *Attorney, Agent, or Firm* — Brinks Gilson & Lione

(57) ABSTRACT

The present invention relates to the 3-arylquinazolin-4-one compounds of the formula I and the salts thereof,

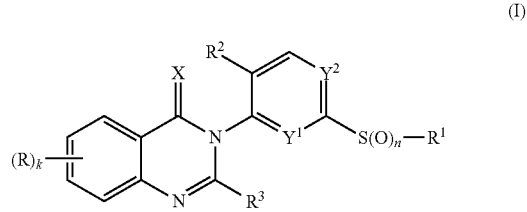

(I)

wherein
n is 0, 1 or 2;
X is O, S or N—$R^4$;
$Y^1$ is N or CH;
$Y^2$ is N or C—$R^5$;
$R^1$ is $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, $C_3$-$C_{12}$-cycloalkyl, $C_5$-$C_{12}$-cycloalkenyl, $C_3$-$C_{12}$-cycloalkyl-$C_1$-$C_4$-alkyl, $C_5$-$C_{12}$-cycloalkenyl-$C_1$-$C_4$-alkyl, where the cycloalkyl radical and the cycloalkenyl radical in the last four mentioned radicals are unsubstituted, partially or fully halogenated and/or carry 1, 2, 3, 4, or 5 $C_1$-$C_4$-alkyl radicals;
$R^2$ is hydrogen, halogen, CN, C(Z)NH$_2$, $C_1$-$C_4$-alkyl or $C_1$-$C_4$-haloalkyl, wherein Z is O, S or NR$^6$;
and the variables k, R, $R^3$, $R^4$, $R^5$ and $R^6$ are as defined in the claims.

The invention also relates to the use of novel compounds of formula I for combating invertebrate pests and to a method for controlling invertebrate pests. The invention also relates to a plant propagation material and to an agricultural composition comprising a 3-arylquinazolin-4-one compound of formula I.

16 Claims, No Drawings

3-ARYLQUINAZOLIN-4-ONE COMPOUNDS FOR COMBATING INVERTEBRATE PESTS

This application is a National Stage application of International Application No. PCT/EP2010/052693, filed Mar. 3, 2010, which claims the benefit of U.S. Provisional Application No. 61/157,375, filed Mar. 4, 2009, the entire contents of which are hereby incorporated herein by reference.

The present invention relates to 3-arylquinazolin-4-one compounds and their use for combating or controlling invertebrate pests, in particular arthropod pests and nematodes. The invention also relates to a method for controlling invertebrate pests by using these compounds and to a plant propagation material and to an agricultural composition comprising said compounds.

BACKGROUND OF THE INVENTION

Invertebrate pests and in particular arthropods and nematodes destroy growing and harvested crops and attack wooden dwellings and commercial structures, causing large economic loss to the food supply and to property. While a large number of pesticidal agents are known, due to the ability of target pests to develop resistance to said agents, there is an ongoing need for new agents for combating invertebrate pests, in particular insects, arachnids and nematodes.

The DE 19547475 describes 3-(2,4-dioxo-pyrimidin-3-yl)-6-cyano-phenyl sulfide derivatives and their applications for protecting crops against harmful insects and weeds.

The US 2006/0106042 describes 2-(4,4-difluoro-but-3-enylsulfanyl)-pyrimidines that may carry heterocyclic groups and their sulfinyl and sulfonyl derivatives. Also described is the activity of these compounds against insects, arachnids and nematodes.

The U.S. Pat. No. 6,509,354 describes 3-(4-oxo-pyrimidin-3-yl)-phenyl sulfide derivatives and their activities against various insect and mite pests.

The pesticidal activities of the compounds of prior art, in particular their activities against arachnids such as mites are not always satisfactory. Moreover, there is an ongoing need for further pesticidal compounds for the reasons outlined above.

Therefore, it is an object of the present invention to provide compounds that have a good pesticidal activity, in particular insecticidal activity, and show a broad activity spectrum against a large number of different invertebrate pests, especially against difficult to control arthropod pests and/or nematodes.

SUMMARY OF THE INVENTION

It has been found that these objectives can be achieved by compounds of the formulae I below and by their salts, in particular their agriculturally or veterinarily acceptable salts.

Therefore, in a first aspect, the invention relates to the 3-arylquinazolin-4-one compounds of formula I:

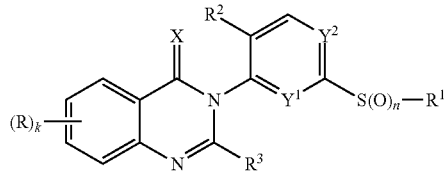

(I)

wherein
k is 0, 1, 2, 3 or 4;
n is 0, 1 or 2;
X is O, S or N—$R^4$;
$Y^1$ is N or CH;
$Y^2$ is N or C—$R^5$;
R is selected from the group consisting of halogen, CN, $NO_2$, $C_1$-$C_4$-alkyl, $C_1$-$C_4$-haloalkyl, $C_2$-$C_4$-alkenyl, $C_1$-$C_4$-haloalkenyl, $C_2$-$C_4$-alkynyl, $C_1$-$C_4$-haloalkynyl, $C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl and $C_1$-$C_4$-haloalkylsulfonyl, for k being 2, 3 or 4 it being possible that R is identical or different;
$R^1$ is $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, $C_3$-$C_{12}$-cycloalkyl, $C_5$-$C_{12}$-cycloalkenyl, $C_3$-$C_{12}$-cycloalkyl-$C_1$-$C_4$-alkyl, $C_5$-$C_{12}$-cycloalkenyl-$C_1$-$C_4$-alkyl, where the cycloalkyl radical and the cycloalkenyl radical in the last four mentioned radicals are unsubstituted, partially or fully halogenated and/or carry 1, 2, 3, 4, or 5 $C_1$-$C_4$-alkyl radicals;
$R^2$ is hydrogen, halogen, CN, C(Z)$NH_2$, $C_1$-$C_4$-alkyl or $C_1$-$C_4$-haloalkyl, wherein Z is O, S or $NR^6$;
$R^3$ is hydrogen, OH, halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl or $C_1$-$C_4$-haloalkylsulfonyl;
$R^4$ is selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_3$-$C_6$-cycloalkyl, $C_5$-$C_6$-cycloalkenyl, $C_3$-$C_6$-cycloalkyl-$C_1$-$C_4$-alkyl, $C_6$-$C_6$-cycloalkenyl-$C_1$-$C_4$-alkyl, $C_3$-$C_6$-cycloalkoxy, $C_5$-$C_6$-cycloalkenoxy, $C_3$-$C_6$-cycloalkyl-$C_1$-$C_4$-alkoxy, $C_5$-$C_6$-cycloalkenyl-$C_1$-$C_4$-alkoxy, where the cycloalkyl radical and the cycloalkenyl radical in the last eight mentioned radicals are unsubstituted, partially or fully halogenated and/or carry 1, 2, 3, 4, or 5 $C_1$-$C_4$-alkyl radicals, phenyl, phenyl-$C_1$-$C_4$-alkyl, phenyloxy and phenyl-$C_1$-$C_4$-alkoxy, wherein the phenyl ring of phenyl, phenyl-$C_1$-$C_4$-alkyl, phenyl-$C_1$-$C_4$-alkoxy and phenoxy is un-substituted or substituted by 1, 2, 3, 4 or 5 substituents selected from halogen, $C_1$-$C_4$-haloalkyl, $C_1$-$C_4$-alkoxy and $C_1$-$C_4$-haloalkoxy; and
$R^5$ is hydrogen, halogen, CN, C(Z)$NH_2$, $C_1$-$C_4$-alkyl or $C_1$-$C_4$-haloalkyl, wherein Z is O, S or $NR^6$;
$R^6$ has one of the meanings given for $R^4$;
and the salts thereof, in particular the agriculturally acceptable salts thereof.

The invention also relates to the use of the 3-arylquinazolin-4-one compounds of formula I as defined above and/or agriculturally acceptable salts thereof for combating invertebrate pests, in particular insects, acaridae and/or nematodes.

The present invention also provides an agricultural composition comprising at least one 3-arylquinazolin-4-one compound of the formula I as defined herein and/or an agriculturally acceptable salt thereof and at least one liquid or solid carrier.

The present invention also provides a method for combating invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a 3-arylquinazolin-4-one compound of formula I or a salt thereof as defined herein.

The present invention also relates to plant propagation material, in particular seed, comprising at least one compound of formula I and/or an agriculturally acceptable salt thereof as defined herein.

The present invention further relates to a method for treating or protecting an animal from infestation or infection by parasites which comprises bringing the animal in contact with a parasiticidally effective amount of a 3-arylquinazolin-4-one compound of the formula I or a veterinarily acceptable salt thereof as defined herein. Bringing the animal in contact with the compound I, its salt or the veterinary composition of the invention means applying or administering it to the animal.

DETAILED DESCRIPTION OF THE INVENTION

Depending on the substitution pattern, the compounds of the formula I may have one or more centers of chirality, in which case they are present as mixtures of enantiomers or diastereomers. The invention provides both the pure enantiomers or diastereomers and their mixtures and the use according to the invention of the pure enantiomers or diastereomers of the compound I or its mixtures. Suitable compounds of the formula I also include all possible stereoisomers (cis/trans isomers) and mixtures thereof.

The compounds of the present invention may be amorphous or may exist in one or more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzltriethylammonium, furthermore phosphonium ions, sulfonium ions, preferably tri($C_1$-$C_4$-alkyl) sulfonium, and sulfoxonium ions, preferably tri($C_1$-$C_4$-alkyl) sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" as used herein includes all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "plants" comprises any types of plants including "non-cultivated plants" and in particular "cultivated plants".

The term "non-cultivated plants" refers to any wild type species or related species or related genera of a cultivated plant.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transational modification of protein(s) (oligo- or polypeptides) poly for example by glycosylation or polymer additions such as prenylated, acetylated or farnesylated moieties or PEG moieties (e.g. as disclosed in Biotechnol Prog. 2001 JulAug; 17(4):720-8., Protein Eng Des Sel. 2004 January; 17(1):57-66, Nat. Protoc. 2007; 2(5):1225-35., Curr. Opin. Chem. Biol. 2006 October; 10(5):487-91. Epub 2006 Aug. 28., Biomaterials. 2001 March; 22(5):405-17, Bioconjug. Chem. 2005 January-February; 16(1):113-21).

The term "cultivated plants" as used herein further includes plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No.

6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" as used herein further includes plants that are by the use of recombinant DNA techniques capable to synthesize one or more insecticidal proteins, especially those known from the bacterial genus *bacillus*, particularly from *bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods insects, particularly to beetles (Coleoptera), flies (Diptera), and butterflies and moths (Lepidoptera) and to plant parasitic nematodes (Nematoda).

The term "cultivated plants" as used herein further includes plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora* infestans derived from the Mexican wild potato *Solanum bulbocastanum*) or T4-lyso-zym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" as used herein further includes plants that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

The term "cultivated plants" as used herein further includes plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" as used herein further includes plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "$C_1$-$C_{10}$-alkyl" as used herein and in the alkyl moieties of alkoxy, alkoxyalkyl, alkylthio, alkylsulfinyl, alkylsulfonyl and the like refers to saturated straight-chain or branched hydrocarbon radicals having 1 to 2, 1 to 4, 1 to 6, 1 to 8 or 1 to 10 carbon atoms. $C_1$-$C_2$-Alkyl is methyl or ethyl. $C_1$-$C_4$-Alkyl is additionally also, for example, propyl, isopropyl, butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof.

The term "$C_1$-$C_{10}$-haloalkyl" as used herein and in the haloalkyl moieties of haloalkoxy, haloalkylthio, haloalkylsulfinyl, haloalkylsulfonyl and the like refers to straight-chain or branched alkyl groups having 1 to 2, 1 to 4, 1 to 6, 1 to 8 or 1 to 10 carbon atoms (as mentioned above), where some or all of the hydrogen atoms in these groups may be replaced by halogen atoms as mentioned above: in particular $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2,2,3,3-tetrafluoropropyl, 3,3-difluoropropyl, 2,3,3-trifluoropropyl, 2,2,3,3,3-pentafluoropropyl, 4,4-difluorobutyl, 4,4,4-trifluorobutyl, 3,4,4-trifluorobutyl, 3,3,4,4-tetrafluorobutyl, 3,3,4,4,4-pentafluorobutyl or 1,1,1-trifluoroprop-2-yl. The term "$C_1$-$C_{10}$-haloalkyl" in particular refers to "$C_1$-$C_4$-fluoroalkyl".

The term "$C_1$-$C_4$-fluoroalkyl" or "fluorinated $C_1$-$C_4$-alkyl" as used herein refers to straight-chain or branched alkyl groups having 1 to 4 carbon atoms (as mentioned above), where some or all of the hydrogen atoms in these groups may be replaced by fluorine atoms: examples include fluoromethyl, difluoromethyl, trifluoromethyl, 1-fluoroethyl, 2-fluoroethyl, 2,2-difluoroethyl, 2,2,2-trifluoroethyl, pentafluoroethyl, 2,2,3,3-tetrafluoropropyl, 3,3-difluoropropyl, 2,3,3-trifluoropropyl, 2,2,3,3,3-pentafluoropropyl, 4,4-difluorobutyl, 4,4,4-trifluorobutyl, 3,4,4-trifluorobutyl, 3,3,4,4-tetrafluorobutyl, 3,3,4,4,4-pentafluorobutyl and 1,1,1-trifluoroprop-2-yl.

The term "$C_2$-$C_{10}$-alkenyl" as used herein and in the alkenyl moiety of alkenyloxy and the like refers to monounsaturated straight-chain or branched hydrocarbon radicals having 2 to 4, 2 to 6, 2 to 8, 3 to 8, 2 to 10 or 3 to 10 carbon atoms and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "$C_2$-$C_{10}$-haloalkenyl" as used herein and the haloalkenyl moieties in haloalkenyloxy, haloalkenylcarbonyl and the like refers to unsaturated straight-chain or branched hydrocarbon radicals having 2 to 4, 2 to 6, 2 to 8 or 2 to 10 carbon atoms and a double bond in any position (as mentioned above), where some or all of the hydrogen atoms in these groups may be replaced by halogen atoms as mentioned above, in particular fluorine, chlorine and bromine, for example 2-chlorovinyl, 2-chloroallyl (2-chloro-2-propen-1-yl), 3-chloro-2-propen-1-yl, 3,3-dichloro-2-propen-1-yl, 2-fluorovinyl, 2,2-fluorovinyl, 3,3-difluoro-2-propen-1-yl, 2,3,3-trifluoro-2-propen-1-yl, 4,4-difluoro-3-buten-1-yl, 3,4,4-trifluoro-3-buten-1-yl and the like; The term "$C_2$-$C_{10}$-haloalkenyl" in particular refers to "$C_2$-$C_4$-fluoroalkenyl".

The term "$C_2$-$C_4$-fluoroalkenyl" or "fluorinated $C_2$-$C_4$-alkenyl" as used herein refers to straight-chain or branched alkenyl groups having 2 to 4 carbon atoms (as mentioned above), where some or all of the hydrogen atoms in these groups may be replaced by fluorine atoms; examples include: 2-fluorovinyl, 2,2-fluorovinyl, 3,3-difluoro-2-propen-1-yl, 2,3,3-trifluoro-2-propen-1-yl, 4,4-difluoro-3-buten-1-yl and 3,4,4-trifluoro-3-buten-1-yl.

The term "$C_2$-$C_{10}$-alkynyl" as used herein and the alkynyl moieties in alkynyloxy, alkynylcarbonyl and the like refers to straight-chain or branched hydrocarbon groups having 2 to 4, 2 to 6, 2 to 8, 3 to 8, 2 to 10 or 3 to 10 carbon atoms and one or two triple bonds in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "$C_2$-$C_{10}$-haloalkynyl" as used herein and the haloalkynyl moieties in haloalkynyloxy, haloalkynylcarbonyl and the like refers to unsaturated straight-chain or branched hydrocarbon radicals having 3 to 4, 3 to 6, 3 to 8 or 3 to 10 carbon atoms and one or two triple bonds in any position (as mentioned above), where some or all of the hydrogen atoms in these groups may be replaced by halogen atoms as mentioned above, in particular fluorine, chlorine and bromine;

The term "$C_3$-$C_{12}$-cycloalkyl" as used herein and in the cycloalkyl moieties of $C_3$-$C_{12}$-cycloalkyl-$C_1$-$C_4$-alkyl and $C_3$-$C_6$-cycloalkyl-$C_1$-$C_4$-alkoxy refers to mono- or bi- or polycyclic, in particular monocyclic saturated hydrocarbon radicals having 3 to 12 (=$C_3$-$C_{12}$-cycloalkyl) carbon atoms, frequently 3 to 8 carbon atoms (=$C_3$-$C_8$-cycloalkyl), in particular 3 to 6 carbon atoms (=$C_3$-$C_6$-cycloalkyl). Examples of monocyclic radicals comprise cyclopropyl, cyclobutyl, cyclopentyl, cyclohexyl, cycloheptyl, cyclooctyl, cyclononyl and cyclodecyl. Examples of bicyclic radicals comprise bicyclo[2.2.1]heptyl, bicyclo[3.1.1]heptyl, bicyclo[2.2.2]octyl and bicyclo[3.2.1]octyl.

The term "$C_3$-$C_{12}$-cycloalkyl-$C_1$-$C_4$-alkyl" as used herein refers to a linear or branched $C_1$-$C_4$-alkyl radical as defined above, which is substituted by an $C_3$-$C_{12}$-cycloalkyl radical, in particular to $C_3$-$C_{12}$-cycloalkyl-$CH_2$, $C_3$-$C_{12}$-cycloalkyl-$CH_2CH_2$ and $C_3$-$C_{12}$-cycloalkyl-$CH(CH_3)$, examples being cyclopropylmethyl (cyclopropyl-$CH_2$), cyclobutylmethyl, cyclopentylmethyl and cyclohexylmethyl.

The term "$C_5$-$C_{12}$-cycloalkenyl" as used and in the cycloalkenyl moieties of $C_5$-$C_{12}$-cycloalkenyl-$C_1$-$C_4$-alkyl refers to mono- or bi- or polycyclic, in particular monocyclic unsaturated hydrocarbon radicals having 5 to 12 (=$C_5$-$C_{12}$-cycloalkenyl), in particular 5 to 8 (=$C_5$-$C_8$-cycloalkenyl) or 5 to 6 (=$C_5$-$C_6$-cycloalkenyl) carbon ring members, such as cyclopenten-1-yl, cyclopenten-3-yl, cyclohexen-1-yl, cyclohexen-3-yl, cyclohexen-4-yl, cycloheptenyl, cyclooctenyl, bicyclo[2.2.2]octenyl and the like.

The term "$C_5$-$C_{12}$-cycloalkenyl-$C_1$-$C_4$-alkyl" as used herein refers to a linear or branched $C_1$-$C_4$-alkyl radical as defined above, which is substituted by an $C_5$-$C_{12}$-cycloalkenyl radical, in particular to $C_5$-$C_{12}$-cycloalkenyl-$CH_2$, $C_3$-$C_{12}$-cycloalkenyl-$CH_2CH_2$ and $C_3$-$C_{12}$-cycloalkenyl-CH ($CH_3$).

The term "$C_1$-$C_4$-alkoxy" as used herein and in the alkoxy moieties of alkoxyalkyl refers to saturated straight-chain or branched hydrocarbon radicals having 1 to 4 carbon atoms which are bound to the remainder of the molecule via an oxygen atom. $C_1$-$C_2$-Alkoxy is methoxy or ethoxy. $C_1$-$C_4$-Alkoxy is additionally also, for example, propoxy, isopropoxy, butoxy, 1-methylpropoxy (sec-butoxy), 2-methylpropoxy (isobutoxy) or 1,1-dimethylethoxy (tert-butoxy).

The term "$C_3$-$C_6$-cycloalkyl-$C_1$-$C_4$-alkoxy" as used herein refers to a linear or branched $C_1$-$C_4$-alkoxyx radical as defined above, which is substituted by an $C_3$-$C_6$-cycloalkyl radical, in particular to $C_3$-$C_{12}$-cycloalkyl-$CH_2O$, $C_3$-$C_{12}$-cycloalkyl-$CH_2CH_2O$ and $C_3$-$C_{12}$-cycloalkyl-CH($CH_3$)O, examples being cyclopropylmethoxy (cyclopropyl-$CH_2$), cyclobutylmethoxy, cyclopentylmethoxy and cyclohexylmethoxy.

The term "$C_1$-$C_4$-alkylthio" as used herein refers alkyl radicals as defined above having 1 to 4 carbon atoms which are bound to the remainder of the molecule via a sulphur atom; examples being methylthio, ethylthio, n-propylthio, isopropylthio, n-butylthio and tert.-butylthio.

The term "$C_1$-$C_4$-alkylsulfonyl" as used herein refers alkyl radicals as defined above having 1 to 4 carbon atoms which are bound to the remainder of the molecule via a $S(O)_2$ group; examples being methylsulfonyl, ethylsulfonyl, n-propylsulfonyl, isopropylsulfonyl, n-butylsulfonyl and tert.-butylsulfonyl.

The term "$C_1$-$C_4$-alkylsulfinyl" as used herein refers alkyl radicals as defined above having 1 to 4 carbon atoms which are bound to the remainder of the molecule via a S(O) group; examples being methylsulfinyl, ethylsulfinyl, n-propylsulfinyl, isopropylsulfinyl, n-butylsulfinyl and tert.-butylsulfinyl.

The term "$C_1$-$C_4$-haloalkoxy" as used herein refers haloalkyl radicals as defined above having 1 to 4 carbon atoms which are bound to the remainder of the molecule via an oxygen atom groups having 1 to 4 carbon atoms (as mentioned above), where some or all of the hydrogen atoms in these groups may be replaced by fluorine atoms: examples include fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, pentafluoroethoxy, 2,2,3,3-tetrafluoropropoxy, 3,3-difluoropropoxy, 2,3,3-trifluoropropoxy, 2,2,3,3,3-pentafluoropropoxy, 4,4-difluorobutoxy, 4,4,4-trifluorobutoxy, 3,4,4-trifluorobutoxy, 3,3,4,4-tetrafluorobutoxy, 3,3,4,4,4-pentafluorobutoxy and 1,1,1-trifluoroprop-2-yloxy.

The term "$C_1$-$C_4$-haloalkylthio" as used herein refers haloalkyl radicals as defined above having 1 to 4 carbon atoms which are bound to the remainder of the molecule via a sulphur atom: examples include fluoromethylthio, difluoromethylthio, trifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, pentafluoroethylthio, 2,2,3,3-tetrafluoropropylthio, 3,3-difluoropropylthio, 2,3,3-trifluoropropylthio, 2,2,3,3,3-pentafluoropropylthio, 4,4-difluorobutylthio, 4,4,4-trifluorobutylthio, 3,4,4-trifluorobutylthio, 3,3,4,4-tetrafluorobutylthio, 3,3,4,4,4-pentafluorobutylthio and 1,1,1-trifluoroprop-2-ylthio.

The term "$C_1$-$C_4$-haloalkylsulfonyl" as used herein refers haloalkyl radicals as defined above having 1 to 4 carbon atoms which are bound to the remainder of the molecule via a $S(O)_2$ group; examples include fluoromethylsulfonyl, difluoromethylsulfonyl, trifluoromethylsulfonyl, 1-fluoroethylsulfonyl, 2-fluoroethylsulfonyl, 2,2-difluoroethylsulfonyl, 2,2,2-trifluoroethylsulfonyl, pentafluoroethylsulfonyl, 2,2,3,3-tetrafluoropropylsulfonyl, 3,3-difluoropropylsulfonyl, 2,3,3-trifluoropropylsulfonyl, 2,2,3,3,3-pentafluoropropylsulfonyl, 4,4-difluorobutylsulfonyl, 4,4,4-trifluorobutylsulfonyl, 3,4,4-trifluorobutylsulfonyl, 3,3,4,4-tetrafluorobutylsulfonyl, 3,3,4,4,4-pentafluorobutylsulfonyl and 1,1,1-trifluoroprop-2-ylsulfonyl.

The term "$C_1$-$C_4$-haloalkylsulfinyl" as used herein refers haloalkyl radicals as defined above having 1 to 4 carbon atoms which are bound to the remainder of the molecule via a S(O) group; examples include fluoromethylsulfinyl, difluoromethylsulfinyl, trifluoromethylsulfinyl, 1-fluoroethylsulfinyl, 2-fluoroethylsulfinyl, 2,2-difluoroethylsulfinyl, 2,2,2-trifluoroethylsulfinyl, pentafluoroethylsulfinyl, 2,2,3,3-tetrafluoropropylsulfinyl, 3,3-difluoropropylsulfinyl, 2,3,3-trifluoropropylsulfinyl, 2,2,3,3,3-pentafluoropropylsulfinyl, 4,4-difluorobutylsulfinyl, 4,4,4-trifluorobutylsulfinyl, 3,4,4-trifluorobutylsulfinyl, 3,3,4,4-tetrafluorobutylsulfinyl, 3,3,4,4-pentafluorobutylsulfinyl and 1,1,1-trifluoroprop-2-ylsulfinyl.

The term "$C_1$-$C_4$-alkoxy-$C_1$-$C_4$-alkyl" as used herein refers to a linear or branched $C_1$-$C_4$-alkyl radical as defined above, which is substituted by an $C_1$-$C_4$-alkoxy radical, in particular to methoxymethyl, ethoxymethyl, n-propoxymethyl, n-butoxyethyl, 2-methoxyethyl, 2-ethoxyethyl, 2-(n-propoxy)ethyl, 2-(n-butoxy)ethyl, 2-methoxypropyl, 2-ethoxypropyl, 2-(n-propoxy)propyl, 2-(n-butoxy)propyl, 3-methoxypropyl, 3-ethoxypropyl, 3-(n-propoxy)propyl, 3-(n-butoxy)propyl, 4-methoxybutyl and 4-ethoxybutyl.

The term "phenyl-$C_1$-$C_4$-alkyl" as used herein refers to a linear or branched $C_1$-$C_4$-alkyl radical as defined above, which is substituted by a phenyl radical: examples include benzyl, 1-phenylethyl and 2-phenylethyl.

The term "phenyl-$C_1$-$C_4$-alkoxy" as used herein refers to a linear or branched $C_1$-$C_4$-alkoxy radical as defined above, which is substituted by a phenyl radical: examples include benzyloxy, 1-phenylethyloxy and 2-phenylethyloxy.

The remarks made below concerning preferred embodiments of the variables of the compounds of formula I, of the features of the use and method according to the invention and of the composition of the invention are valid on their own as well as preferably in combination with each other.

Preferred are 3-arylquinazolin-4-one compounds of formula I, wherein $R^1$ is selected from the group consisting of $C_1$-$C_4$-alkyl, fluorinated $C_1$-$C_4$-alkyl, $C_2$-$C_4$-alkenyl, fluorinated $C_2$-$C_4$-alkenyl, cyclopropyl and cyclopropylmethyl. Particularly preferred are compounds of formula I, wherein $R^1$ is fluorinated $C_1$-$C_4$-alkyl or fluorinated $C_2$-$C_4$-alkenyl. In an especially preferred embodiment, $R^1$ is 2,2,2-trifluoroethyl. In another especially preferred embodiment, $R^1$ is 3,4,4-trifluoro-3-buten-1-yl.

Preference is further given to 3-arylquinazolin-4-one compounds of formula I, wherein $R^2$ is hydrogen, fluorine, chlorine or methyl. Particular preference is given to compounds of formula I, wherein $R^2$ is hydrogen or fluorine.

Also preferred are 3-arylquinazolin-4-one compounds of formula I, wherein $R^3$ is hydrogen.

Preference is further given to 3-arylquinazolin-4-one compounds of formula I, wherein k is 0.

Likewise, preference is given to 3-arylquinazolin-4-one compounds of formula I, wherein k is 1, 2 or 3, in particular 1 and wherein each R is independently selected from fluorine, chlorine, CN, $NO_2$, methyl and methoxy.

A particular preferred embodiment of the invention relates to compounds of the formula I, wherein the variable X is O.

Another embodiment of the invention relates to compounds of the formula I, wherein the variable X is S.

A further embodiment of the invention relates to compounds of the formula I, wherein the variable X is N—$R^4$. In this embodiment $R^4$ is preferably selected from the group consisting of $C_1$-$C_4$-alkyl, $C_1$-$C_4$-alkoxy, $C_2$-$C_4$-alkenyl and $C_2$-$C_4$-alkenyloxy.

Preference is also given to compounds of formula I, wherein the variable $Y^1$ is CH and the variable $Y^2$ is C—$R^5$. Preferred meanings of $R^5$ are hydrogen, chlorine, methyl, difluoromethyl, trifluoromethyl or cyano, in particular hydrogen or methyl.

Likewise, preference is given to compounds of formula I, wherein $Y^1$ and $Y^2$ are both N.

In a preferred embodiment of the invention, the variable n is 0.

In another preferred embodiment of the invention, the variable n is 1.

In a further preferred embodiment of the invention, the variable n is 2.

A preferred embodiment of the invention relates to the compounds I of formula I-A:

(I-A)

wherein R, $R^1$, $R^2$, $R^3$, $R^5$, X, n and k have one of the meanings given above, especially one of the preferred meanings.

Especially preferred are compounds of formula I-A having the following meanings:
k is 0, 1, 2, or 3, in particular 0 or 1;
n is 0, 1 or 2;
X is O;
R if present, is identical or different and selected from fluorine, chlorine, CN, $NO_2$, methyl and methoxy;
$R^1$ is $C_1$-$C_4$-alkyl, fluorinated $C_1$-$C_4$-alkyl, $C_2$-$C_4$-alkenyl, fluorinated $C_2$-$C_4$-alkenyl, $C_2$-$C_{10}$-alkynyl, cyclopropyl or cyclopropylmethyl, more preferably fluorinated $C_1$-$C_4$-alkyl or fluorinated $C_2$-$C_4$-alkenyl, in particular 2,2,2-trifluoroethyl or 3,4,4-trifluoro-3-buten-1-yl;
$R^2$ is hydrogen, fluorine, chlorine or methyl, in particular fluorine or chlorine;
$R^3$ is hydrogen; and
$R^5$ is hydrogen, chlorine, methyl, difluoromethyl, trifluoromethyl or CN, in particular hydrogen or methyl.

A further preferred embodiment of the invention relates to the compounds I of formula I-B:

(I-B)

wherein R, $R^1$, $R^2$, $R^3$, X, n and k have one of the meanings given above, especially one of the preferred meanings.

Especially preferred are compounds of formula I-B having the following meanings:
k is 0, 1, 2, or 3, in particular 0 or 1;
n is 0, 1 or 2;
X is O;
R if present, is identical or different and selected from fluorine, chlorine, CN, $NO_2$, methyl and methoxy;
$R^1$ is $C_1$-$C_4$-alkyl, fluorinated $C_1$-$C_4$-alkyl, $C_2$-$C_4$-alkenyl, fluorinated $C_2$-$C_4$-alkenyl, $C_2$-$C_{10}$-alkynyl, cyclopropyl or cyclopropylmethyl, more preferably fluorinated $C_1$-$C_4$-alkyl or fluorinated $C_2$-$C_4$-alkenyl, in particular 2,2,2-trifluoroethyl or 3,4,4-trifluoro-3-buten-1-yl;
$R^2$ is hydrogen, fluorine, chlorine or methyl, in particular fluorine or chlorine, especially hydrogen; and
$R^3$ is hydrogen.

In particular with a view to their use for combating invertebrate pests, preference is given to the individual compounds of the formula I-A (compounds of formula I-A, where X is O, $R^3$ is H) and the variables n, k, R, $R^1$, $R^2$ and $R^5$ each have the meanings, in particular the preferred meanings given above.

(I-A')

Examples of the compounds I-A' are compiled in tables 1 to 29 below, where the variables n, $R^1$, $R^2$ and $R^5$ each have the meanings given in one row of table A.

TABLE A

|  | $R^1$ | $R^2$ | $R^5$ | n |
|---|---|---|---|---|
| A-1 | methyl | H | Cl | 0 |
| A-2 | ethyl | H | Cl | 0 |
| A-3 | trifluoromethyl | H | Cl | 0 |
| A-4 | n-propyl | H | Cl | 0 |
| A-5 | cyclopropyl | H | Cl | 0 |
| A-6 | methylcyclopropyl | H | Cl | 0 |
| A-7 | cyclopropylmethyl | H | Cl | 0 |
| A-8 | 2,2,2-trifluoroethyl | H | Cl | 0 |
| A-9 | 3,4,4-trifluoro-3-buten-1-yl | H | Cl | 0 |
| A-10 | methyl | H | $CH_3$ | 0 |
| A-11 | ethyl | H | $CH_3$ | 0 |
| A-12 | trifluoromethyl | H | $CH_3$ | 0 |
| A-13 | n-propyl | H | $CH_3$ | 0 |
| A-14 | cyclopropyl | H | $CH_3$ | 0 |
| A-15 | methylcyclopropyl | H | $CH_3$ | 0 |
| A-16 | cyclopropylmethyl | H | $CH_3$ | 0 |
| A-17 | 2,2,2-trifluoroethyl | H | $CH_3$ | 0 |

TABLE A-continued

| | R¹ | R² | R⁵ | n |
|---|---|---|---|---|
| A-18 | 3,4,4-trifluoro-3-buten-1-yl | H | CH₃ | 0 |
| A-19 | methyl | H | CHF₂ | 0 |
| A-20 | ethyl | H | CHF₂ | 0 |
| A-21 | trifluoromethyl | H | CHF₂ | 0 |
| A-22 | n-propyl | H | CHF₂ | 0 |
| A-23 | cyclopropyl | H | CHF₂ | 0 |
| A-24 | methylcyclopropyl | H | CHF₂ | 0 |
| A-25 | cyclopropylmethyl | H | CHF₂ | 0 |
| A-26 | 2,2,2-trifluoroethyl | H | CHF₂ | 0 |
| A-27 | 3,4,4-trifluoro-3-buten-1-yl | H | CHF₂ | 0 |
| A-28 | methyl | H | CF₃ | 0 |
| A-29 | ethyl | H | CF₃ | 0 |
| A-30 | trifluoromethyl | H | CF₃ | 0 |
| A-31 | n-propyl | H | CF₃ | 0 |
| A-32 | cyclopropyl | H | CF₃ | 0 |
| A-33 | methylcyclopropyl | H | CF₃ | 0 |
| A-34 | cyclopropylmethyl | H | CF₃ | 0 |
| A-35 | 2,2,2-trifluoroethyl | H | CF₃ | 0 |
| A-36 | 3,4,4-trifluoro-3-buten-1-yl | H | CF₃ | 0 |
| A-37 | methyl | H | CN | 0 |
| A-38 | ethyl | H | CN | 0 |
| A-39 | trifluoromethyl | H | CN | 0 |
| A-40 | n-propyl | H | CN | 0 |
| A-41 | cyclopropyl | H | CN | 0 |
| A-42 | methylcyclopropyl | H | CN | 0 |
| A-43 | cyclopropylmethyl | H | CN | 0 |
| A-44 | 2,2,2-trifluoroethyl | H | CN | 0 |
| A-45 | 3,4,4-trifluoro-3-buten-1-yl | H | CN | 0 |
| A-46 | methyl | F | Cl | 0 |
| A-47 | ethyl | F | Cl | 0 |
| A-48 | trifluoromethyl | F | Cl | 0 |
| A-49 | n-propyl | F | Cl | 0 |
| A-50 | cyclopropyl | F | Cl | 0 |
| A-51 | methylcyclopropyl | F | Cl | 0 |
| A-52 | cyclopropylmethyl | F | Cl | 0 |
| A-53 | 2,2,2-trifluoroethyl | F | Cl | 0 |
| A-54 | 3,4,4-trifluoro-3-buten-1-yl | F | Cl | 0 |
| A-55 | methyl | F | CH₃ | 0 |
| A-56 | ethyl | F | CH₃ | 0 |
| A-57 | trifluoromethyl | F | CH₃ | 0 |
| A-58 | n-propyl | F | CH₃ | 0 |
| A-59 | cyclopropyl | F | CH₃ | 0 |
| A-60 | methylcyclopropyl | F | CH₃ | 0 |
| A-61 | cyclopropylmethyl | F | CH₃ | 0 |
| A-62 | 2,2,2-trifluoroethyl | F | CH₃ | 0 |
| A-63 | 3,4,4-trifluoro-3-buten-1-yl | F | CH₃ | 0 |
| A-64 | methyl | F | CHF₂ | 0 |
| A-65 | ethyl | F | CHF₂ | 0 |
| A-66 | trifluoromethyl | F | CHF₂ | 0 |
| A-67 | n-propyl | F | CHF₂ | 0 |
| A-68 | cyclopropyl | F | CHF₂ | 0 |
| A-69 | methylcyclopropyl | F | CHF₂ | 0 |
| A-70 | cyclopropylmethyl | F | CHF₂ | 0 |
| A-71 | 2,2,2-trifluoroethyl | F | CHF₂ | 0 |
| A-72 | 3,4,4-trifluoro-3-buten-1-yl | F | CHF₂ | 0 |
| A-73 | methyl | F | CF₃ | 0 |
| A-74 | ethyl | F | CF₃ | 0 |
| A-75 | trifluoromethyl | F | CF₃ | 0 |
| A-76 | n-propyl | F | CF₃ | 0 |
| A-77 | cyclopropyl | F | CF₃ | 0 |
| A-78 | methylcyclopropyl | F | CF₃ | 0 |
| A-79 | cyclopropylmethyl | F | CF₃ | 0 |
| A-80 | 2,2,2-trifluoroethyl | F | CF₃ | 0 |
| A-81 | 3,4,4-trifluoro-3-buten-1-yl | F | CF₃ | 0 |
| A-82 | methyl | F | CN | 0 |
| A-83 | ethyl | F | CN | 0 |
| A-84 | trifluoromethyl | F | CN | 0 |
| A-85 | n-propyl | F | CN | 0 |
| A-86 | cyclopropyl | F | CN | 0 |
| A-87 | methylcyclopropyl | F | CN | 0 |
| A-88 | cyclopropylmethyl | F | CN | 0 |
| A-89 | 2,2,2-trifluoroethyl | F | CN | 0 |
| A-90 | 3,4,4-trifluoro-3-buten-1-yl | F | CN | 0 |
| A-91 | methyl | H | Cl | 1 |
| A-92 | ethyl | H | Cl | 1 |
| A-93 | trifluoromethyl | H | Cl | 1 |
| A-94 | n-propyl | H | Cl | 1 |
| A-95 | cyclopropyl | H | Cl | 1 |
| A-96 | methylcyclopropyl | H | Cl | 1 |
| A-97 | cyclopropylmethyl | H | Cl | 1 |
| A-98 | 2,2,2-trifluoroethyl | H | Cl | 1 |
| A-99 | 3,4,4-trifluoro-3-buten-1-yl | H | Cl | 1 |
| A-100 | methyl | H | CH₃ | 1 |
| A-101 | ethyl | H | CH₃ | 1 |
| A-102 | trifluoromethyl | H | CH₃ | 1 |
| A-103 | n-propyl | H | CH₃ | 1 |
| A-104 | cyclopropyl | H | CH₃ | 1 |
| A-105 | methylcyclopropyl | H | CH₃ | 1 |
| A-106 | cyclopropylmethyl | H | CH₃ | 1 |
| A-107 | 2,2,2-trifluoroethyl | H | CH₃ | 1 |
| A-108 | 3,4,4-trifluoro-3-buten-1-yl | H | CH₃ | 1 |
| A-109 | methyl | H | CHF₂ | 1 |
| A-110 | ethyl | H | CHF₂ | 1 |
| A-111 | trifluoromethyl | H | CHF₂ | 1 |
| A-112 | n-propyl | H | CHF₂ | 1 |
| A-113 | cyclopropyl | H | CHF₂ | 1 |
| A-114 | methylcyclopropyl | H | CHF₂ | 1 |
| A-115 | cyclopropylmethyl | H | CHF₂ | 1 |
| A-116 | 2,2,2-trifluoroethyl | H | CHF₂ | 1 |
| A-117 | 3,4,4-trifluoro-3-buten-1-yl | H | CHF₂ | 1 |
| A-118 | methyl | H | CF₃ | 1 |
| A-119 | ethyl | H | CF₃ | 1 |
| A-120 | trifluoromethyl | H | CF₃ | 1 |
| A-121 | n-propyl | H | CF₃ | 1 |
| A-122 | cyclopropyl | H | CF₃ | 1 |
| A-123 | methylcyclopropyl | H | CF₃ | 1 |
| A-124 | cyclopropylmethyl | H | CF₃ | 1 |
| A-125 | 2,2,2-trifluoroethyl | H | CF₃ | 1 |
| A-126 | 3,4,4-trifluoro-3-buten-1-yl | H | CF₃ | 1 |
| A-127 | methyl | H | CN | 1 |
| A-128 | ethyl | H | CN | 1 |
| A-129 | trifluoromethyl | H | CN | 1 |
| A-130 | n-propyl | H | CN | 1 |
| A-131 | cyclopropyl | H | CN | 1 |
| A-132 | methylcyclopropyl | H | CN | 1 |
| A-133 | cyclopropylmethyl | H | CN | 1 |
| A-134 | 2,2,2-trifluoroethyl | H | CN | 1 |
| A-135 | 3,4,4-trifluoro-3-buten-1-yl | H | CN | 1 |
| A-136 | methyl | F | Cl | 1 |
| A-137 | ethyl | F | Cl | 1 |
| A-138 | trifluoromethyl | F | Cl | 1 |
| A-139 | n-propyl | F | Cl | 1 |
| A-140 | cyclopropyl | F | Cl | 1 |
| A-141 | methylcyclopropyl | F | Cl | 1 |
| A-142 | cyclopropylmethyl | F | Cl | 1 |
| A-143 | 2,2,2-trifluoroethyl | F | Cl | 1 |
| A-144 | 3,4,4-trifluoro-3-buten-1-yl | F | Cl | 1 |
| A-145 | methyl | F | CH₃ | 1 |
| A-146 | ethyl | F | CH₃ | 1 |
| A-147 | trifluoromethyl | F | CH₃ | 1 |
| A-148 | n-propyl | F | CH₃ | 1 |
| A-149 | cyclopropyl | F | CH₃ | 1 |
| A-150 | methylcyclopropyl | F | CH₃ | 1 |
| A-151 | cyclopropylmethyl | F | CH₃ | 1 |
| A-152 | 2,2,2-trifluoroethyl | F | CH₃ | 1 |
| A-153 | 3,4,4-trifluoro-3-buten-1-yl | F | CH₃ | 1 |
| A-154 | methyl | F | CHF₂ | 1 |
| A-155 | ethyl | F | CHF₂ | 1 |
| A-156 | trifluoromethyl | F | CHF₂ | 1 |
| A-157 | n-propyl | F | CHF₂ | 1 |
| A-158 | cyclopropyl | F | CHF₂ | 1 |
| A-159 | methylcyclopropyl | F | CHF₂ | 1 |
| A-160 | cyclopropylmethyl | F | CHF₂ | 1 |
| A-161 | 2,2,2-trifluoroethyl | F | CHF₂ | 1 |
| A-162 | 3,4,4-trifluoro-3-buten-1-yl | F | CHF₂ | 1 |
| A-163 | methyl | F | CF₃ | 1 |
| A-164 | ethyl | F | CF₃ | 1 |
| A-165 | trifluoromethyl | F | CF₃ | 1 |
| A-166 | n-propyl | F | CF₃ | 1 |
| A-167 | cyclopropyl | F | CF₃ | 1 |
| A-168 | methylcyclopropyl | F | CF₃ | 1 |
| A-169 | cyclopropylmethyl | F | CF₃ | 1 |
| A-170 | 2,2,2-trifluoroethyl | F | CF₃ | 1 |
| A-171 | 3,4,4-trifluoro-3-buten-1-yl | F | CF₃ | 1 |
| A-172 | methyl | F | CN | 1 |
| A-173 | ethyl | F | CN | 1 |

TABLE A-continued

| | R¹ | R² | R⁵ | n |
|---|---|---|---|---|
| A-174 | trifluoromethyl | F | CN | 1 |
| A-175 | n-propyl | F | CN | 1 |
| A-176 | cyclopropyl | F | CN | 1 |
| A-177 | methylcyclopropyl | F | CN | 1 |
| A-178 | cyclopropylmethyl | F | CN | 1 |
| A-179 | 2,2,2-trifluoroethyl | F | CN | 1 |
| A-180 | 3,4,4-trifluoro-3-buten-1-yl | F | CN | 1 |
| A-181 | methyl | H | Cl | 2 |
| A-182 | ethyl | H | Cl | 2 |
| A-183 | trifluoromethyl | H | Cl | 2 |
| A-184 | n-propyl | H | Cl | 2 |
| A-185 | cyclopropyl | H | Cl | 2 |
| A-186 | methylcyclopropyl | H | Cl | 2 |
| A-187 | cyclopropylmethyl | H | Cl | 2 |
| A-188 | 2,2,2-trifluoroethyl | H | Cl | 2 |
| A-189 | 3,4,4-trifluoro-3-buten-1-yl | H | Cl | 2 |
| A-190 | methyl | H | $CH_3$ | 2 |
| A-191 | ethyl | H | $CH_3$ | 2 |
| A-192 | trifluoromethyl | H | $CH_3$ | 2 |
| A-193 | n-propyl | H | $CH_3$ | 2 |
| A-194 | cyclopropyl | H | $CH_3$ | 2 |
| A-195 | methylcyclopropyl | H | $CH_3$ | 2 |
| A-196 | cyclopropylmethyl | H | $CH_3$ | 2 |
| A-197 | 2,2,2-trifluoroethyl | H | $CH_3$ | 2 |
| A-198 | 3,4,4-trifluoro-3-buten-1-yl | H | $CH_3$ | 2 |
| A-199 | methyl | H | $CHF_2$ | 2 |
| A-200 | ethyl | H | $CHF_2$ | 2 |
| A-201 | trifluoromethyl | H | $CHF_2$ | 2 |
| A-202 | n-propyl | H | $CHF_2$ | 2 |
| A-203 | cyclopropyl | H | $CHF_2$ | 2 |
| A-204 | methylcyclopropyl | H | $CHF_2$ | 2 |
| A-205 | cyclopropylmethyl | H | $CHF_2$ | 2 |
| A-206 | 2,2,2-trifluoroethyl | H | $CHF_2$ | 2 |
| A-207 | 3,4,4-trifluoro-3-buten-1-yl | H | $CHF_2$ | 2 |
| A-208 | methyl | H | $CF_3$ | 2 |
| A-209 | ethyl | H | $CF_3$ | 2 |
| A-210 | trifluoromethyl | H | $CF_3$ | 2 |
| A-211 | n-propyl | H | $CF_3$ | 2 |
| A-212 | cyclopropyl | H | $CF_3$ | 2 |
| A-213 | methylcyclopropyl | H | $CF_3$ | 2 |
| A-214 | cyclopropylmethyl | H | $CF_3$ | 2 |
| A-215 | 2,2,2-trifluoroethyl | H | $CF_3$ | 2 |
| A-216 | 3,4,4-trifluoro-3-buten-1-yl | H | $CF_3$ | 2 |
| A-217 | methyl | H | CN | 2 |
| A-218 | ethyl | H | CN | 2 |
| A-219 | trifluoromethyl | H | CN | 2 |
| A-220 | n-propyl | H | CN | 2 |
| A-221 | cyclopropyl | H | CN | 2 |
| A-222 | methylcyclopropyl | H | CN | 2 |
| A-223 | cyclopropylmethyl | H | CN | 2 |
| A-224 | 2,2,2-trifluoroethyl | H | CN | 2 |
| A-225 | 3,4,4-trifluoro-3-buten-1-yl | H | CN | 2 |
| A-226 | methyl | F | Cl | 2 |
| A-227 | ethyl | F | Cl | 2 |
| A-228 | trifluoromethyl | F | Cl | 2 |
| A-229 | n-propyl | F | Cl | 2 |
| A-230 | cyclopropyl | F | Cl | 2 |
| A-231 | methylcyclopropyl | F | Cl | 2 |
| A-232 | cyclopropylmethyl | F | Cl | 2 |
| A-233 | 2,2,2-trifluoroethyl | F | Cl | 2 |
| A-234 | 3,4,4-trifluoro-3-buten-1-yl | F | Cl | 2 |
| A-235 | methyl | F | $CH_3$ | 2 |
| A-236 | ethyl | F | $CH_3$ | 2 |
| A-237 | trifluoromethyl | F | $CH_3$ | 2 |
| A-238 | n-propyl | F | $CH_3$ | 2 |
| A-239 | cyclopropyl | F | $CH_3$ | 2 |
| A-240 | methylcyclopropyl | F | $CH_3$ | 2 |
| A-241 | cyclopropylmethyl | F | $CH_3$ | 2 |
| A-242 | 2,2,2-trifluoroethyl | F | $CH_3$ | 2 |
| A-243 | 3,4,4-trifluoro-3-buten-1-yl | F | $CH_3$ | 2 |
| A-244 | methyl | F | $CHF_2$ | 2 |
| A-245 | ethyl | F | $CHF_2$ | 2 |
| A-246 | trifluoromethyl | F | $CHF_2$ | 2 |
| A-247 | n-propyl | F | $CHF_2$ | 2 |
| A-248 | cyclopropyl | F | $CHF_2$ | 2 |
| A-249 | methylcyclopropyl | F | $CHF_2$ | 2 |
| A-250 | cyclopropylmethyl | F | $CHF_2$ | 2 |
| A-251 | 2,2,2-trifluoroethyl | F | $CHF_2$ | 2 |
| A-252 | 3,4,4-trifluoro-3-buten-1-yl | F | $CHF_2$ | 2 |
| A-253 | methyl | F | $CF_3$ | 2 |
| A-254 | ethyl | F | $CF_3$ | 2 |
| A-255 | trifluoromethyl | F | $CF_3$ | 2 |
| A-256 | n-propyl | F | $CF_3$ | 2 |
| A-257 | cyclopropyl | F | $CF_3$ | 2 |
| A-258 | methylcyclopropyl | F | $CF_3$ | 2 |
| A-259 | cyclopropylmethyl | F | $CF_3$ | 2 |
| A-260 | 2,2,2-trifluoroethyl | F | $CF_3$ | 2 |
| A-261 | 3,4,4-trifluoro-3-buten-1-yl | F | $CF_3$ | 2 |
| A-262 | methyl | F | CN | 2 |
| A-263 | ethyl | F | CN | 2 |
| A-264 | trifluoromethyl | F | CN | 2 |
| A-265 | n-propyl | F | CN | 2 |
| A-266 | cyclopropyl | F | CN | 2 |
| A-267 | methylcyclopropyl | F | CN | 2 |
| A-268 | cyclopropylmethyl | F | CN | 2 |
| A-269 | 2,2,2-trifluoroethyl | F | CN | 2 |
| A-270 | 3,4,4-trifluoro-3-buten-1-yl | F | CN | 2 |
| A-271 | trifluoromethyl | $CH_3$ | $CH_3$ | 0 |
| A-272 | trifluoromethyl | $CH_3$ | $CH_3$ | 1 |
| A-273 | trifluoromethyl | $CH_3$ | $CH_3$ | 2 |
| A-274 | trifluoromethyl | $CH_3$ | CN | 0 |
| A-275 | trifluoromethyl | $CH_3$ | CN | 1 |
| A-276 | trifluoromethyl | $CH_3$ | CN | 2 |
| A-277 | 2,2,2-trifluoroethyl | $CH_3$ | $CH_3$ | 0 |
| A-278 | 2,2,2-trifluoroethyl | $CH_3$ | $CH_3$ | 1 |
| A-279 | 2,2,2-trifluoroethyl | $CH_3$ | $CH_3$ | 2 |
| A-280 | 2,2,2-trifluoroethyl | $CH_3$ | CN | 0 |
| A-281 | 2,2,2-trifluoroethyl | $CH_3$ | CN | 1 |
| A-282 | 2,2,2-trifluoroethyl | $CH_3$ | CN | 2 |
| A-283 | 3,4,4-trifluoro-3-buten-1-yl | $CH_3$ | $CH_3$ | 0 |
| A-284 | 3,4,4-trifluoro-3-buten-1-yl | $CH_3$ | $CH_3$ | 1 |
| A-285 | 3,4,4-trifluoro-3-buten-1-yl | $CH_3$ | $CH_3$ | 2 |
| A-286 | 3,4,4-trifluoro-3-buten-1-yl | $CH_3$ | CN | 0 |
| A-287 | 3,4,4-trifluoro-3-buten-1-yl | $CH_3$ | CN | 1 |
| A-288 | 3,4,4-trifluoro-3-buten-1-yl | $CH_3$ | CN | 2 |

Table 1:

Compounds of the formula I-A', in which k is 0 and the combination of n, $R^1$, $R^2$ and $R^5$ for each individual compound corresponds in each case to one row of table A.

Table 2:

Compounds of the formula I-A', in which k is 1, $(R)_k$ is 5-$NO_2$ and the combination of n, $R^1$, $R^2$ and $R^5$ for each individual compound corresponds in each case to one row of table A.

Table 3:

Compounds of the formula I-A', in which k is 1, $(R)_k$ is 6-$NO_2$ and the combination of n, $R^1$, $R^2$ and $R^5$ for each individual compound corresponds in each case to one row of table A.

Table 4:

Compounds of the formula I-A', in which k is 1, $(R)_k$ is 7-$NO_2$ and the combination of n, $R^1$, $R^2$ and $R^5$ for each individual compound corresponds in each case to one row of table A.

Table 5:

Compounds of the formula I-A', in which k is 1, $(R)_k$ is 8-$NO_2$ and the combination of n, $R^1$, $R^2$ and $R^5$ for each individual compound corresponds in each case to one row of table A.

Table 6:

Compounds of the formula I-A', in which k is 1, $(R)_k$ is 5-CN and the combination of n, $R^1$, $R^2$ and $R^5$ for each individual compound corresponds in each case to one row of table A.

Table 7:

Compounds of the formula I-A', in which k is 1, $(R)_k$ is 6-CN and the combination of n, $R^1$, $R^2$ and $R^5$ for each individual compound corresponds in each case to one row of table A.

Table 8:
Compounds of the formula I-A', in which k is 1, $(R)_k$ is 7-CN and the combination of n, $R^1$, $R^2$ and $R^5$ for each individual compound corresponds in each case to one row of table A.

Table 9:
Compounds of the formula I-A', in which k is 1, $(R)_k$ is 8-CN and the combination of n, $R^1$, $R^2$ and $R^5$ for each individual compound corresponds in each case to one row of table A.

Table 10:
Compounds of the formula I-A', in which k is 1, $(R)_k$ is 5-$CH_3$ and the combination of n, $R^1$, $R^2$ and $R^5$ for each individual compound corresponds in each case to one row of table A.

Table 11:
Compounds of the formula I-A', in which k is 1, $(R)_k$ is 6-$CH_3$ and the combination of n, $R^1$, $R^2$ and $R^5$ for each individual compound corresponds in each case to one row of table A.

Table 12:
Compounds of the formula I-A', in which k is 1, $(R)_k$ is 7-$CH_3$ and the combination of n, $R^1$, $R^2$ and $R^5$ for each individual compound corresponds in each case to one row of table A.

Table 13:
Compounds of the formula I-A', in which k is 1, $(R)_k$ is 8-$CH_3$ and the combination of n, $R^1$, $R^2$ and $R^5$ for each individual compound corresponds in each case to one row of table A.

Table 14:
Compounds of the formula I-A', in which k is 1, $(R)_k$ is 5-$CF_3$ and the combination of n, $R^1$, $R^2$ and $R^5$ for each individual compound corresponds in each case to one row of table A.

Table 15:
Compounds of the formula I-A', in which k is 1, $(R)_k$ is 6-$CF_3$ and the combination of n, $R^1$, $R^2$ and $R^5$ for each individual compound corresponds in each case to one row of table A.

Table 16:
Compounds of the formula I-A', in which k is 1, $(R)_k$ is 7-$CF_3$ and the combination of n, $R^1$, $R^2$ and $R^5$ for each individual compound corresponds in each case to one row of table A.

Table 17:
Compounds of the formula I-A', in which k is 1, $(R)_k$ is 8-$CF_3$ and the combination of n, $R^1$, $R^2$ and $R^5$ for each individual compound corresponds in each case to one row of table A.

Table 18:
Compounds of the formula I-A', in which k is 1, $(R)_k$ is 5-Cl and the combination of n, $R^1$, $R^2$ and $R^5$ for each individual compound corresponds in each case to one row of table A.

Table 19:
Compounds of the formula I-A', in which k is 1, $(R)_k$ is 6-Cl and the combination of n, $R^1$, $R^2$ and $R^5$ for each individual compound corresponds in each case to one row of table A.

Table 20:
Compounds of the formula I-A', in which k is 1, $(R)_k$ is 7-Cl and the combination of n, $R^1$, $R^2$ and $R^5$ for each individual compound corresponds in each case to one row of table A.

Table 21:
Compounds of the formula I-A', in which k is 1, $(R)_k$ is 8-Cl and the combination of n, $R^1$, $R^2$ and $R^5$ for each individual compound corresponds in each case to one row of table A.

Table 22:
Compounds of the formula I-A', in which k is 1, $(R)_k$ is 5-$OCH_3$ and the combination of n, $R^1$, $R^2$ and $R^5$ for each individual compound corresponds in each case to one row of table A.

Table 23:
Compounds of the formula I-A', in which k is 1, $(R)_k$ is 6-$OCH_3$ and the combination of n, $R^1$, $R^2$ and $R^5$ for each individual compound corresponds in each case to one row of table A.

Table 24:
Compounds of the formula I-A', in which k is 1, $(R)_k$ is 7-$OCH_3$ and the combination of n, $R^1$, $R^2$ and $R^5$ for each individual compound corresponds in each case to one row of table A.

Table 25:
Compounds of the formula I-A', in which k is 1, $(R)_k$ is 8-$OCH_3$ and the combination of n, $R^1$, $R^2$ and $R^5$ for each individual compound corresponds in each case to one row of table A.

Table 26:
Compounds of the formula I-A', in which k is 1, $(R)_k$ is 5-F and the combination of n, $R^1$, $R^2$ and $R^5$ for each individual compound corresponds in each case to one row of table A.

Table 27:
Compounds of the formula I-A', in which k is 1, $(R)_k$ is 6-F and the combination of n, $R^1$, $R^2$ and $R^5$ for each individual compound corresponds in each case to one row of table A.

Table 28:
Compounds of the formula I-A', in which k is 1, $(R)_k$ is 7-F and the combination of n, $R^1$, $R^2$ and $R^5$ for each individual compound corresponds in each case to one row of table A.

Table 29:
Compounds of the formula I-A', in which k is 1, $(R)_k$ is 8-F and the combination of n, $R^1$, $R^2$ and $R^5$ for each individual compound corresponds in each case to one row of table A.

In particular with a view to their use for combating invertebrate pests, preference is given to the individual compounds of the formula I-B' (compounds of formula I-B, where X is O, $R^3$ is H) and the variables n, k, R, $R^1$ and $R^2$ each have the meanings, in particular the preferred meanings given above.

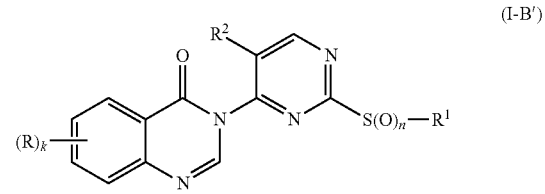

(I-B')

Examples of the compounds I-B' are compiled in tables 30 to 58 below, where the variables n, $R^1$ and $R^2$ each have the meanings given in one row of table B.

TABLE B

| | $R^1$ | $R^2$ | n |
|---|---|---|---|
| B-1 | methyl | H | 0 |
| B-2 | ethyl | H | 0 |
| B-3 | trifluoromethyl | H | 0 |
| B-4 | n-propyl | H | 0 |
| B-5 | cyclopropyl | H | 0 |
| B-6 | methylcyclopropyl | H | 0 |
| B-7 | cyclopropylmethyl | H | 0 |
| B-8 | 2,2,2-trifluoroethyl | H | 0 |
| B-9 | 3,4,4-trifluoro-3-buten-1-yl | H | 0 |

TABLE B-continued

|   | R¹ | R² | n |
|---|---|---|---|
| B-10 | methyl | H | 1 |
| B-11 | ethyl | H | 1 |
| B-12 | trifluoromethyl | H | 1 |
| B-13 | n-propyl | H | 1 |
| B-14 | cyclopropyl | H | 1 |
| B-15 | methylcyclopropyl | H | 1 |
| B-16 | cyclopropylmethyl | H | 1 |
| B-17 | 2,2,2-trifluoroethyl | H | 1 |
| B-18 | 3,4,4-trifluoro-3-buten-1-yl | H | 1 |
| B-19 | methyl | H | 2 |
| B-20 | ethyl | H | 2 |
| B-21 | trifluoromethyl | H | 2 |
| B-22 | n-propyl | H | 2 |
| B-23 | cyclopropyl | H | 2 |
| B-24 | methylcyclopropyl | H | 2 |
| B-25 | cyclopropylmethyl | H | 2 |
| B-26 | 2,2,2-trifluoroethyl | H | 2 |
| B-27 | 3,4,4-trifluoro-3-buten-1-yl | H | 2 |
| B-28 | methyl | F | 0 |
| B-29 | ethyl | F | 0 |
| B-30 | trifluoromethyl | F | 0 |
| B-31 | n-propyl | F | 0 |
| B-32 | cyclopropyl | F | 0 |
| B-33 | methylcyclopropyl | F | 0 |
| B-34 | cyclopropylmethyl | F | 0 |
| B-35 | 2,2,2-trifluoroethyl | F | 0 |
| B-36 | 3,4,4-trifluoro-3-buten-1-yl | F | 0 |
| B-37 | methyl | F | 1 |
| B-38 | ethyl | F | 1 |
| B-39 | trifluoromethyl | F | 1 |
| B-40 | n-propyl | F | 1 |
| B-41 | cyclopropyl | F | 1 |
| B-42 | methylcyclopropyl | F | 1 |
| B-43 | cyclopropylmethyl | F | 1 |
| B-44 | 2,2,2-trifluoroethyl | F | 1 |
| B-45 | 3,4,4-trifluoro-3-buten-1-yl | F | 1 |
| B-46 | methyl | F | 2 |
| B-47 | ethyl | F | 2 |
| B-48 | trifluoromethyl | F | 2 |
| B-49 | n-propyl | F | 2 |
| B-50 | cyclopropyl | F | 2 |
| B-51 | methylcyclopropyl | F | 2 |
| B-52 | cyclopropylmethyl | F | 2 |
| B-53 | 2,2,2-trifluoroethyl | F | 2 |
| B-54 | 3,4,4-trifluoro-3-buten-1-yl | F | 2 |
| B-55 | trifluoromethyl | $CH_3$ | 0 |
| B-56 | 2,2,2-trifluoroethyl | $CH_3$ | 0 |
| B-57 | 3,4,4-trifluoro-3-buten-1-yl | $CH_3$ | 0 |
| B-58 | trifluoromethyl | $CH_3$ | 1 |
| B-59 | 2,2,2-trifluoroethyl | $CH_3$ | 1 |
| B-60 | 3,4,4-trifluoro-3-buten-1-yl | $CH_3$ | 1 |
| B-61 | trifluoromethyl | $CH_3$ | 2 |
| B-62 | 2,2,2-trifluoroethyl | $CH_3$ | 2 |
| B-63 | 3,4,4-trifluoro-3-buten-1-yl | $CH_3$ | 2 |

Table 30:
Compounds of the formula I-B', in which k is 0 and the combination of n, $R^1$ and $R^2$ for each individual compound corresponds in each case to one row of table B.

Table 31:
Compounds of the formula I-B', in which k is 1, $(R)_k$ is 5-$NO_2$ and the combination of n, $R^1$ and $R^2$ for each individual compound corresponds in each case to one row of table B.

Table 32:
Compounds of the formula I-B', in which k is 1, $(R)_k$ is 6-$NO_2$ and the combination of n, $R^1$ and $R^2$ for each individual compound corresponds in each case to one row of table B.

Table 33:
Compounds of the formula I-B', in which k is 1, $(R)_k$ is 7-$NO_2$ and the combination of n, $R^1$ and $R^2$ for each individual compound corresponds in each case to one row of table B.

Table 34:
Compounds of the formula I-B', in which k is 1, $(R)_k$ is 8-$NO_2$ and the combination of n, $R^1$ and $R^2$ for each individual compound corresponds in each case to one row of table B.

Table 35:
Compounds of the formula I-B', in which k is 1, $(R)_k$ is 5-CN and the combination of n, $R^1$ and $R^2$ for each individual compound corresponds in each case to one row of table B.

Table 36:
Compounds of the formula I-B', in which k is 1, $(R)_k$ is 6-CN and the combination of n, $R^1$ and $R^2$ for each individual compound corresponds in each case to one row of table B.

Table 37:
Compounds of the formula I-B', in which k is 1, $(R)_k$ is 7-CN and the combination of n, $R^1$ and $R^2$ for each individual compound corresponds in each case to one row of table B.

Table 38:
Compounds of the formula I-B', in which k is 1, $(R)_k$ is 8-CN and the combination of n, $R^1$ and $R^2$ for each individual compound corresponds in each case to one row of table B.

Table 39:
Compounds of the formula I-B', in which k is 1, $(R)_k$ is 5-$CH_3$ and the combination of n, $R^1$ and $R^2$ for each individual compound corresponds in each case to one row of table B.

Table 40:
Compounds of the formula I-B', in which k is 1, $(R)_k$ is 6-$CH_3$ and the combination of n, $R^1$ and $R^2$ for each individual compound corresponds in each case to one row of table B.

Table 41:
Compounds of the formula I-B', in which k is 1, $(R)_k$ is 7-$CH_3$ and the combination of n, $R^1$ and $R^2$ for each individual compound corresponds in each case to one row of table B.

Table 42:
Compounds of the formula I-B', in which k is 1, $(R)_k$ is 8-$CH_3$ and the combination of n, $R^1$ and $R^2$ for each individual compound corresponds in each case to one row of table B.

Table 43:
Compounds of the formula I-B', in which k is 1, $(R)_k$ is 5-$CF_3$ and the combination of n, $R^1$ and $R^2$ for each individual compound corresponds in each case to one row of table B.

Table 44:
Compounds of the formula I-B', in which k is 1, $(R)_k$ is 6-$CF_3$ and the combination of n, $R^1$ and $R^2$ for each individual compound corresponds in each case to one row of table B.

Table 45:
Compounds of the formula I-B', in which k is 1, $(R)_k$ is 7-$CF_3$ and the combination of n, $R^1$ and $R^2$ for each individual compound corresponds in each case to one row of table B.

Table 46:
Compounds of the formula I-B', in which k is 1, $(R)_k$ is 8-$CF_3$ and the combination of n, $R^1$ and $R^2$ for each individual compound corresponds in each case to one row of table B.

Table 47:
Compounds of the formula I-B', in which k is 1, $(R)_k$ is 5-Cl and the combination of n, $R^1$ and $R^2$ for each individual compound corresponds in each case to one row of table B.

Table 48:
Compounds of the formula I-B', in which k is 1, $(R)_k$ is 6-Cl and the combination of n, $R^1$ and $R^2$ for each individual compound corresponds in each case to one row of table B.

Table 49:
Compounds of the formula I-B', in which k is 1, $(R)_k$ is 7-Cl and the combination of n, $R^1$ and $R^2$ for each individual compound corresponds in each case to one row of table B.

Table 50:

Compounds of the formula I-B', in which k is 1, $(R)_k$ is 8-Cl and the combination of n, $R^1$ and $R^2$ for each individual compound corresponds in each case to one row of table B.

Table 51:

Compounds of the formula I-B', in which k is 1, $(R)_k$ is 5-OCH$_3$ and the combination of n, $R^1$ and $R^2$ for each individual compound corresponds in each case to one row of table B.

Table 52:

Compounds of the formula I-B', in which k is 1, $(R)_k$ is 6-OCH$_3$ and the combination of n, $R^1$ and $R^2$ for each individual compound corresponds in each case to one row of table B.

Table 53:

Compounds of the formula I-B', in which k is 1, $(R)_k$ is 7-OCH$_3$ and the combination of n, $R^1$ and $R^2$ for each individual compound corresponds in each case to one row of table B.

Table 54:

Compounds of the formula I-B', in which k is 1, $(R)_k$ is 8-OCH$_3$ and the combination of n, $R^1$ and $R^2$ for each individual compound corresponds in each case to one row of table B.

Table 55:

Compounds of the formula I-B', in which k is 1, $(R)_k$ is 5-F and the combination of n, $R^1$ and $R^2$ for each individual compound corresponds in each case to one row of table B.

Table 56:

Compounds of the formula I-B', in which k is 1, $(R)_k$ is 6-F and the combination of n, $R^1$ and $R^2$ for each individual compound corresponds in each case to one row of table B.

Table 57:

Compounds of the formula I-B', in which k is 1, $(R)_k$ is 7-F and the combination of n, $R^1$ and $R^2$ for each individual compound corresponds in each case to one row of table B.

Table 58:

Compounds of the formula I-B', in which k is 1, $(R)_k$ is 8-F and the combination of n, $R^1$ and $R^2$ for each individual compound corresponds in each case to one row of table B.

Preparation of the compounds of formula I can be accomplished according to standard methods of organic chemistry, e.g. by the methods described hereinafter or in the working examples but are not limited to the routes given below.

The compounds of formula I wherein n equals 0, can for instance be prepared according to the method depicted in scheme 1 by a reduction of the nitro compound of the formula II followed by a condensation reaction of the obtained amine compound with an ortho ester $R_3$—C(O—$R^a$)$_3$.

Scheme 1:

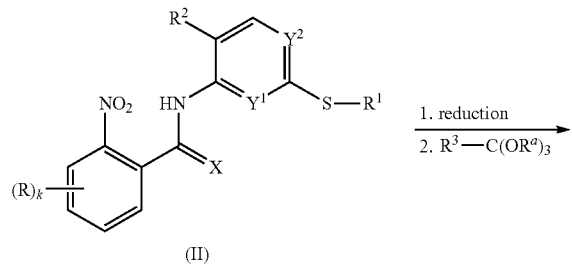

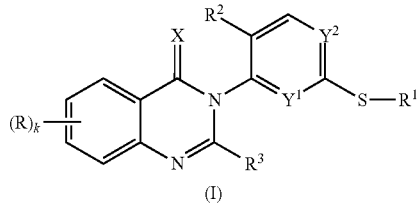

In scheme 1, k, R, $R^1$, $R^2$, $R^3$, $Y^1$, $Y^2$ and X have one of the meanings given above and $R^a$ preferably denotes a $C_1$-$C_4$-alkyl group, such as methyl or ethyl. X is preferably O.

According to scheme 1, the nitro group of a compound II is first reduced to an amino group by methods well known in the art, such as hydrogenation in the presence of Raney nickel. According to the second step depicted in scheme 1 an $R^3$-substituted methyne group is introduced bridging the secondary nitrogen atom of the amide group and the nitrogen atom of the newly formed amino group to yield a compound I. This conversion can be achieved for instance by reacting with an ortho ester such as triethoxymethane or 1,1,1-triethoxyethane.

The compounds of formula I wherein n equals 1, can for instance be prepared by oxidation of the corresponding compound I wherein n equals 0 using an oxidation reagent such as diluted nitric acid, hydrogen peroxide, or a peroxy acid, for example metachloroperoxybenzoic acid.

The compounds of formula I wherein n equals 2, can for instance be prepared by oxidation of a corresponding compound I wherein n equals 0 or 1 using concentrated nitric acid, potassium permanganate or an excess of either hydrogen peroxide or peroxy acid.

The compounds of formula I wherein X is S can for instance be prepared by thionation of the corresponding compound I wherein X is O using phosphorus pentasulfide or Lawesson's reagent. Alternatively S can be introduced in position X by such a thionation reaction at an earlier or later stage of the synthesis, for example by thionation of compound II.

Compounds of formula I, wherein X is N—$R^4$, can be prepared e.g. by reacting a compound of formula I, wherein X is S, with the corresponding amine $R^4$—NH$_2$ in accordance to the method described by V. Glushkov et al. in Pharmaceutical Chemistry Journal 2005, 39(10), 533-536.

Compounds of formula II wherein X is O can for instance be prepared according to the method depicted in scheme 2 by an acylation reaction.

Scheme 2

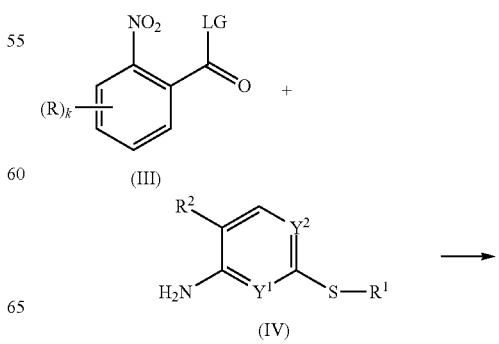

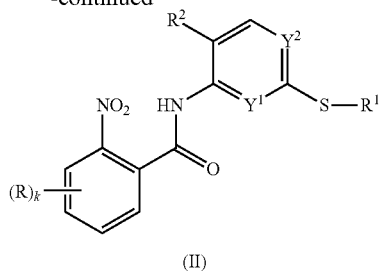

(II)

In scheme 2, k, R, $R^1$, $R^2$, $Y^1$, $Y^2$ and X have one of the meanings given above and LG denotes a leaving group such as halogen, $C_1$-$C_6$-alkoxy or hydroxy.

According to scheme 2 compound IV is reacted with a carboxylic acid of formula III, or an ester thereof or a carboxylic acid halogenide, especially chloride, thereof by methods familiar to an organic chemist and well known in the art to give a compound of formula II.

Compounds of the formulae IV are known, e.g. from JP 2007284356 or can be prepared in analogy to the methods described there. They can for example be prepared from compounds VI as outlined in scheme 3 below.

Scheme 3:

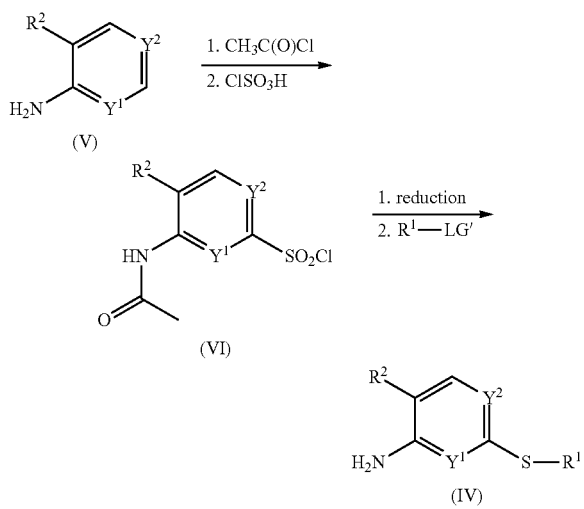

In scheme 3, $R^1$, $R^2$, $Y^1$ and $Y^2$ have one of the meanings given above and LG' denotes a leaving group such as halogen, e.g. bromine or iodine.

According to the method outlined in scheme 3, the (het) aryl sulfonylchloride VI is first reduced to the corresponding thiol by conventional means, for instance by reacting with hydroiodic acid or $LiAlH_4$. As outlined in scheme 3, the thiol is then converted into the thioester IV by conventional means, for instance by reacting with a haloalkyl iodide, in case a haloalkyl is intended as radical $R^1$. Typically, the latter step is carried out in the presence of a reducing agent such as sodium hydroxymethylsulfinate (Rongalite®, BASF) in order to convert dithiol that may have been formed from two molecules of compound VI during the preceding reduction step, to the corresponding thiol.

The (het)aryl sulfonylchlorides VI can for example be prepared according to the method outlined in scheme 3, by reacting an aryl amine V, subsequent to the introduction of an amino protecting group, with chlorosulfonic acid.

Compounds of the formula IV, wherein $Y^1$ and W are N, can be prepared according to the following scheme 4:

Scheme 4:

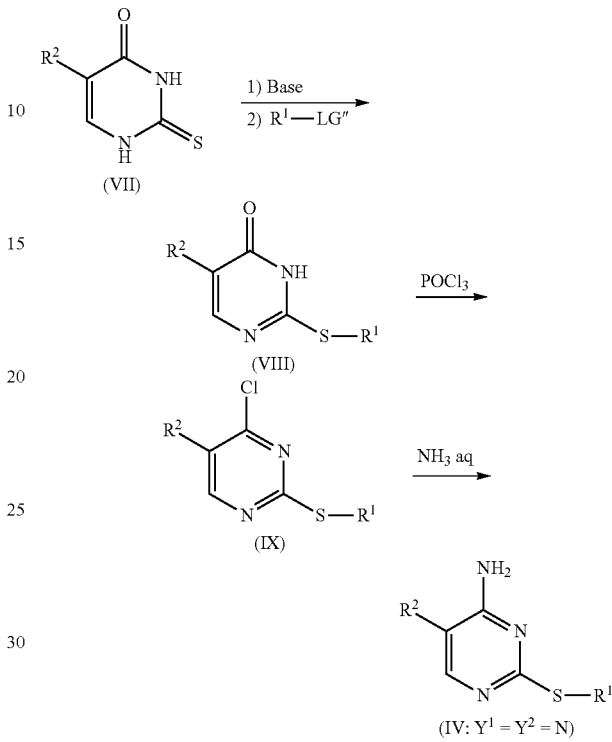

In scheme 4, $R^1$ and $R^2$ have one of the meanings given above and LG" denotes a leaving group such as halogen, e.g. bromine or iodine.

According to scheme 4, a 2-thioxo-2,3-dihydropyrimidin-4-one compound VII is first converted to the corresponding sulfanyl compound VIII by conventional means, for instance by reacting with a haloalkyl halide such as a haloalkyl iodide, in case a haloalkyl radical is intended as radical $R^1$. Typically this step is performed in the presence of a base such as an alkaline earth metal hydride or alkaline metal hydride, e.g. sodium hydride. Compound VIII is then converted to a 4-chloropyrimidine compound IX by reacting with phosphorus oxychloride. Finally, compound IX is reacted with aqueous ammonia to give the compound IV.

(Het)aryl amines of formula V are known in the art (e.g. 4-methylaniline, CAS number [106-49-0] and 4-aminopyrimidine, CAS number [59-54-8]) or they can be prepared by methods familiar to an organic chemist and well known in the art. Suitable methods for preparing compounds V comprise inter alia the catalytic reduction of the corresponding aryl nitro compounds (see e.g. Chemistry Letters 1975, 4, 259-260).

Several of the compounds III and III', such as 2-nitro benzoic acid and 2-nitro benzonitrile, are commercially available.

As a rule, the compounds of formula I can be prepared by the methods described above. If individual compounds cannot be prepared via the above-described routes, they can be prepared by derivatization of other compounds of formula I or by customary modifications of the synthesis routes described. For example, in individual cases, certain compounds of formula I can advantageously be prepared from other compounds of formula I by ester hydrolysis, amidation, esterification, ether cleavage, olefination, reduction, metal catalyzed coupling reactions, oxidation and the like.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization.

Due to their excellent activity, the compounds of formula I may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt thereof or a composition as defined above.

Preferably, the method of the invention serves for protecting plant propagation material (such as seed) and the plant which grows therefrom from animal pest attack or infestation and comprises treating the plant propagation material (such as seed) with a pesticidally effective amount of a compound of the formula I or an agriculturally acceptable salt thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes.

The invention further provides an agricultural composition for combating such invertebrate pests, which comprises such an amount of at least one compound of formula I or at least one agriculturally useful salt thereof and at least one inert liquid and/or solid agronomically acceptable carrier that has a pesticidal action and, if desired, at least one surfactant.

Such a composition may contain a single active compound of formula I or a salt thereof or a mixture of several active compounds of formula I or their salts according to the present invention. The composition according to the present invention may comprise an individual isomer or mixtures of isomers as well as individual tautomers or mixtures of tautomers.

The compounds of the formula I and the pesticidal compositions comprising them are effective agents for controlling arthropod pests and nematodes. Invertebrate pests controlled by the compounds of formula I include for example:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus suicatus, Otiorrhynchus ovatus, Phaedon cochleariae, Phyllotreta chrysocephala, Phyilophaga sp., Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifoiii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adeiges laricis, Aphidula nasturtii, Aphis fabae, Aphis forbesi, Aphis pomi, Aphis gossypii, Aphis grossulariae, Aphis schneideri, Aphis spiraecoia, Aphis sambuci, Acyrthosiphon pisum, Aulacorthum solani, Bemisia argentifolii, Brachycaudus cardui, Brachycaudus helichrysi, Brachcaudus ersicae, Brachycaudus prunicola, Brevicoryne brassicae, Capitophorus horni, Cerosipha gossypii, Chaetosiphon fragaefoiii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand*, and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubats, Otobius megnini, Dermanyssus gallinae, Psoroptes ovis, Rhipicephalus appendiculatus, Rhipicephalus evertsi, Sarcoptes scabiei*, and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri*, and *oligonychus pratensis;*

Siphonatera, e.g. *Xenopsylla cheopsis, Ceratophyllus* spp;

The compositions and compounds of formula I are useful for the control of nematodes, especially plant parasitic nematodes such as root knot nematodes, *Meloidogyne hapla, Meloidogyne incognita, Meloidogyne javanica*, and other *Meloidogyne* species;

cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species;

Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Heliocotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formula I are used for controlling insects or arachnids, in particular insects of the orders Lepidoptera, Coleoptera, Thysanoptera and Homoptera and arachnids of the order Acarina. The compounds of the formula I according to the present invention are particularly useful for controlling insects of the order Thysanoptera and Homoptera.

The compounds of formula I or the pesticidal compositions comprising them may be used to protect growing plants and crops from attack or infestation by invertebrate pests, especially insects, acaridae or arachnids by contacting the plant/crop with a pesticidally effective amount of compounds of formula I. The term "crop" refers both to growing and harvested crops.

The compounds of formula I can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation Technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2-10 fold leading to concentrations in the ready to use preparations of 0.01 to 60% by weight of active compound, preferably 0.1 to 40% by weight.

The compounds of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10% by weight, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:

1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formula I are also suitable for the treatment of plant propagation materials (such as seed). Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Other preferred FS formulations of compounds of formula I for seed treatment comprise from 0.5 to 80 wt % of the active ingredient, from 0.05 to 5 wt % of a wetter, from 0.5 to 15 wt % of a dispersing agent, from 0.1 to 5 wt % of a thickener, from 5 to 20 wt % of an anti-freeze agent, from 0.1 to 2 wt % of an anti-foam agent, from 1 to 20 wt % of a pigment and/or a dye, from 0 to 15 wt % of a sticker/adhesion agent, from 0 to 75 wt % of a filler/vehicle, and from 0.01 to 1 wt % of a preservative.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact (via soil, glass, wall, bed net, carpet, plant parts or animal parts), and ingestion (bait, or plant part).

For use against ants, termites, wasps, flies, mosquitoes, crickets, or cockroaches, cornpounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g. in spray cans), oil sprays or pump sprays are highly suitable for the non-professional user for controlling pests such as flies, fleas, ticks, mosquitoes or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, xyleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and their respective compositions also comprise treating surfaces of huts and houses, air spraying and impregnation of curtains, tents, clothing items, bed nets, tsetse-fly trap or the like. Insecticidal compositions for application to fibers, fabric, knit goods, nonwovens, netting material or foils and tarpaulins preferably comprise a mixture including the insecticide, optionally a repellent and at least one binder. Suitable repellents for exam-ple are N,N-diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bed nets is done in general by dipping the textile material into emulsions or dispersions of the active compounds of formula I or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formula I into contact with each other, and "seed dressing" to methods of seed treatment which provide the seeds with an amount of the compounds of formula I, i.e. which generate a seed comprising the compound of formula I. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of formula I or the enantiomers or veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the enantiomers or veterinarily acceptable salts thereof or a composition comprising it.

The present invention also provides a non-therapeutic method for treating, controlling, preventing and protecting animals against infestation and infection by parasites, which comprises applying to a locus a parasiticidally effective amount of a compound of formula I or the enantiomers or veterinarily acceptable salts thereof or a composition comprising it.

The invention also provides a process for the preparation of a composition for treating, controlling, preventing or protecting animals against infestation or infection by parasites which comprises including a parasiticidally effective amount of a compound of formula I or the enantiomers or veterinarily acceptable salts thereof in a composition comprising it.

The invention relates further to the use of compounds of formula I for treating, controlling, preventing or protecting animals against infestation or infection by parasites.

The invention relates also to the use of a compound of formula I, or a composition comprising it, for the manufacture of a medicament for the therapeutic treatment of animals against infections or infestations by parasites.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the enantiomers or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating endoparasites.

The compounds of formula I are especially useful for combating parasites of the following orders and species, respectively:

fleas (Siphonaptera), e.g. *Ctenocephalides fells, Ctenocephalides canis, Xenopsylla cheopis, Pulex irritans, Tunga penetrans,* and *Nosopsyllus fasciatus,* cockroaches (Blattaria-Blattodea), e.g. *Blattella germanica, Blattella asahinae, Periplaneta americana, Periplaneta japonica, Periplaneta brunnea, Periplaneta fulgginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborn; Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Cho/sops at/anticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprin, Lucilia cuprina, Lucllia sericata, Lycoria pectoralis, Mansonia* spp., *Musca domestica, Muscina stabulans, Oestrus ovis, Phlebotomus argentipes, Psorophora columbiae, Psorophora discolor, Prosimulium mmixtum, Sarcophaga haemorrhoidalis, Sarcophaga* sp., *Simulium viltatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurystemus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni; Dermacentor variabllis, Amblyomma americanum, Amblyomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectulafius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Wemeckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma resale,*

Intestinal roundworms (Ascaridida), e.g. *Ascaris lumbricoides, Ascaris suum, Ascandia galli; Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna*, *Paragonimus* spp., *Dicrocoelium* spp., *Fasciolopsis buski*, *Clonorchis sinensis*, *Schistosoma* spp., *Trichobilharzia* spp., *Alaria alata*, *Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum*, *Multiceps* spp., *Hymenolepis* spp., *Mesocestades* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

The compounds of formula I can be effective through both contact (via soil, glass, wall, bed net, carpet, blankets or animal parts) and ingestion (e.g. baits).

The present invention relates to the therapeutic and the non-therapeutic use of compounds of formula I for controlling and/or combating parasites in and/or on animals.

The compounds of formula I may be used to protect the animals from attack or infestation by parasites by contacting them with a parasitically effective amount of compounds of formula I. As such, "contacting" includes both direct contact (applying the compounds/compositions directly on the parasite, e.g. also at it's locus, and optionally also administrating the compounds/composition directly on the animal) and indirect contact (applying the compounds/compositions to the locus of the parasite). The contact of the parasite through application to its locus is an example of a non-therapeutic use of compounds of formula I.

"Locus" as defined above means the habitat, food supply, breeding ground, area, material or environment in which a parasite is growing or may grow outside of the animal. The compounds of the invention can also be applied preventively to places at which occurrence of the pests or parasites is expected.

The administration to the animal can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:

liquid paraffins, silicone oils, natural, vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg, preferably 1 mg/kg to 50 mg/kg body weight of the treated animal per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of formula I or the compositions comprising them in the use form as pesticides with other pesticides frequently results in a broader pesticidal spectrum of action.

The following list M of pesticides together with which the compounds according to the invention can be used and with which potential synergistic effects might be produced, is intended to illustrate the possible combinations, but not to impose any limitation:

The following list M of pesticides together with which the compounds according to the invention can be used and with which potential synergistic effects might be produced, is intended to illustrate the possible combinations, but not to impose any limitation:

M.1. Organo(thio)phosphates: acephate, azamethiphos, azinphos-ethyl, azinphosmethyl, chlorethoxyfos, chlorfenvinphos, chlormephos, chlorpyrifos, chlorpyrifosmethyl, coumaphos, cyanophos, demeton-5-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroids: acrinathrin, allethrin, d-cis-trans allethrin, d-trans allethrin, bifenthrin, bioallethrin, bioallethrin S-cylclopentenyl, bioresmethrin, cycloprothrin, cyfluthrin, betacyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide; (R)-, (S)-3-Chlor-N1-{2-methyl-4-[1,2,2,2-tetrafluoro-1-(trifluoromethyl)ethyl]phenyl}-N2-(1-methyl-2-methylsulfonylethyl)phthalamide (M21.1);

M.22. Various: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, 4-But-2-ynyloxy-6-(3,5-dimethyl-piperidin-1-yl)-2-fluoro-pyrimidine (M22.1), 3-Benzoylamino-N-[2,6-dimethyl-4-(1,2,2,2-tetrafluoro-1-trifluoromethyl-ethyl)-phenyl]-2-fluoro-benzamide (M22.2), 4-[5-(3,5-Dichloro-phenyl)-5-trifluoromethyl-4,5-dihydro-isoxazol-3-yl]-2-methyl-N-pyridin-2-ylmethyl-benzamide (M22.3), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.4), 4-[5-(3,5-Dichloro-phenyl)-5-trifluoromethyl-4,5-dihydro-isoxazol-3-yl]-2-methyl-N-thiazol-2-ylmethyl-benzamide (M22.5), 4-[5-(3,5-Dichloro-phenyl)-5-trifluoromethyl-4,5-dihydro-isoxazol-3-yl]-2-methyl-N-(tetrahydro-furan-2-yl-methyl)-benzamide (M22.6), 4-{[(6-Bromopyrid-3-yl)methyl](2-fluoroethyl)amino}furan-2(5H)-on (M22.7), 4-{[(6-Fluoropyrid-3-yl)methyl](2,2-difluoroethyl)amino}furan-2(5H)-on (M22.8), 4-{[(2-Chloro-1,3-thiazolo-5-yl)methyl](2-fluoroethyl)amino}furan-2(5H)-on (M22.9), 4-{[(6-Chloropyrid-3-yl)methyl](2-fluoroethyl)amino}furan-2(5H)-on (M22.10), 4-{[(6-Chloropyrid-3-yl)methyl](2,2-difluoroethyl)amino}furan-2(5H)-on (M22.11), 4-{[(6-Chloro-5-fluoropyrid-3-yl)methyl](methyl)amino}furan-2(5H)-on (M22.12), 4-{[(5,6-Dichloropyrid-3-yl)methyl](2-fluoroethyl)amino}furan-2(5H)-on (M22.13), 4-{[(6-Chloro-5-fluoropyrid-3-yl)methyl](cyclopropyl)amino}furan-2(5H)-on (M22.14), 4-{[(6-Chloropyrid-3-yl)methyl](cyclopropyl)amino}furan-2(5H)-on (M22.15), 4-{[(6-Chloropyrid-3-yl)methyl](methyl)amino}furan-2(5H)-on (M22.16), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-1'-oxo-9-(3-pyridinyl)-2H,11H-naphtho[2,1-b]pyrano[3,4-e]pyran-3,6-diyl]ester (M22.17), 8-(2-Cyclopropylmethoxy-4-methyl-phenoxy)-3-(6-methyl-pyridazin-3-yl)-3-aza-bicyclo[3.2.1]octane (M22.18), M.23. N—R'-2,2-dihalo-1-R"cyclo-propanecarboxamide-2-(2,6-dichloro-α,α,α-trifluoro-p-tolyl)hydrazone or N—R'-2,2-di(R''')propionamide-2-(2,6-dichloro-α,α,α,-trifluoro-p-tolyl)-hydrazone, wherein R' is methyl or ethyl, halo is chloro or bromo, R" is hydrogen or methyl and R''' is methyl or ethyl;

M.24. Anthranilamides: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M24.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M24.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M24.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M24.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M24.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M24.6), M.25. Malononitrile compounds: $CF_2HCF_2CF_2CF_2CH_2C(CN)_2CH_2CH_2CF_3$, (2-(2,2,3,3,4,4,5,5-octafluoropentyl)-2-(3,3,3-trifluoro-propyl)malononitrile), $CF_2HCF_2CF_2CF_2CH_2C(CN)_2CH_2CH_2CF_2CF_3$ (2-(2,2,3,3,4,4,5,5-octafluoropentyl)-2-(3,3,4,4,4-pentafluorobutyl)-malonodinitrile);

M.26. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

The commercially available compounds of the group M may be found in The Pesticide Manual, 13th Edition, British Crop Protection Council (2003) among other publications.

Thioamides of formula M6.1 and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Metaflumizone and its preparation have been described in EP-A1462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chloranthraniliprole has been described in WO 01/70671, WO 03/015519 and WO 05/118552. Cyantraniliprole has been described in WO 01/70671, WO 04/067528 and WO 05/118552. The anthranilamides M 24.1 to M 24.6 have been described in WO 2008/72743 and WO 200872783. The phthalamide M 21.1 is known from WO 2007/101540. Cyflumetofen and its preparation have been described in WO 04/080180. The aminoquinazolinone compound pyrifluquinazon has been described in EP A 109 7932. Sulfoximine sulfoxaflor has been described in WO 2006/060029 and WO 2007/149134. The alkynylether compound M22.1 is described e.g. in JP 2006131529. Organic sulfur compounds have been described in WO 2007060839. The carboxamide compound M 22.2 is known from WO 2007/83394. The oxazoline compounds M 22.3 to M 22.6 have been described in WO 2007/074789. The furanon compounds M 22.7 to M 22.16 have been described e.g. in WO 2007/115644. The pyripyropene derivative M 22.17 has been described in WO 2008/66153 and WO 2008/108491. The pyridazin compound M 22.18 has been described in JP 2008/115155. The malononitrile compounds have been described in WO 02/089579, WO 02/090320, WO 02/090321, WO 04/006677, WO 05/068423, WO 05/068432 and WO 05/063694.

Fungicidal mixing partners are those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, fluoxastrobin, kresoxim-methyl, metominostrobin, orysastrobin, picoxystrobin or trifloxystrobin, sulfenic acid derivatives such as captafol, captan, dichlofluanid, folpet, tolylfluanid, cinnemamides and analogs such as dimethomorph, flumetover or flumorph.

The invertebrate pest, i.e. arthropodes and nematodes, the plant, soil or water in which the plant is growing can be contacted with the present compound(s) of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

Moreover, invertebrate pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

"Locus" means a habitat, breeding ground, cultivated plants, plant propagation material (such as seed), soil, area, material or environment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formula I can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001% by weight to 15% by weight, desirably from 0.001% by weight to 5% by weight of active compound.

For use in spray compositions, the content of active ingredient is from 0.001 to 80% by weight, preferably from 0.01 to 50% by weight and most preferably from 0.01 to 15% by weight.

For use in treating crop plants, the rate of application of the active ingredients of this invention may be in the range of 0.1 g to 4000 g per hectare, desirably from 25 g to 600 g per hectare, more desirably from 50 g to 500 g per hectare.

In the treatment of seed, the application rates of the active ingredients are generally from 0.1 g to 10 kg per 100 kg of seed, preferably from 1 g to 5 kg per 100 kg of seed, in particular from 1 g to 200 g per 100 kg of seed.

The present invention is now illustrated in further detail by the following examples.

I. PREPARATION EXAMPLES

Products were characterized by $^1$H-NMR spectroscopy or HPLC (High Performance Liquid Chromatography Mass Spectrometry). HPLC was carried out using an analytic RP-18 column (Chromolith Speed ROD from Merck KGaA, Germany) which was operated at 40° C. Acetonitrile with 0.1% by volume of a trifluoro acetic acid/water mixture and 0.1% by volume of trifluoroacetic acid served as mobile phase; flow rate: 1.8 mL/min and injection volume: 2 µl.

Example 1

Compound I-1

2-(2,2,2-trifluoroethylsufanyl)-4-(4-oxo-quinazolin-3-yl)-5-fluoro-toluol (Compound of formula I, wherein k is 0, n is 0, $R^1$ is $F_3C-CH_2$, $R^2$ is F, $R^3$ is H, $Y^1$ is CH, $Y^2$ is $C-CH_3$ and X is O)

1.1 3-Acetamino-4-fluoro-6-methyl-phenylsulfonylchloride

To a solution of 2-fluoro-4-methyl-aniline (250 g, 2 mol) and triethylamine (202 g, 2 mol) in 2 L of dichloromethane was added dropwise acetylchloride (156 g, 2 mol). The reaction mixture was stirred for 2 hours at a temperature of 0° C. and subsequently washed with dilute hydrochloric acid. The organic phase was dried with sodium sulfate and concentrated under reduced pressure to yield 2-fluoro-4-methyl-acetanilide as a crude intermediate (334 g, 87%).

To 546 g (3.27 mol) of crude 2-fluoro-4-methyl-acetanilide was added chlorosulphonic acid (2000 g, 17.24 mol) with stirring at a temperature below 70° C. Stirring was continued for 3 hours at a temperature of 70° C. The reaction mixture was poured onto ice and then extracted with ethyl acetate. The organic phase was dried with sodium sulfate and concentrated under reduced pressure to yield the title compound (500 g, 57.8%).

$^1$H NMR (400 MHz, CDCl$_3$): δ=9.1 (d, 1H, J=7.2 Hz), 7.39-7.52 (m, 1H), 7.14 (d, 1H, J=11.2 Hz), 2.72-2.78 (m, 3H), 2.2-2.3 (m, 3H).

1.2 3-(2,2,2-Trifluoroethylsulfanyl)-4-methyl-6-fluoro-aniline

3-Acetamino-4-fluoro-6-methyl-phenylsulfonylchloride (500 g, 1.89 mol) was dissolved in 2 L of acetic acid. Red phosphorus (100 g, 3.22 mmol) and iodine (10 g, 39 mmol) were added to the solution, and the mixture was refluxed for 3 hours. The acetic acid was removed under reduced pressure, water was added and the residue extracted with ethyl acetate. The organic phase was dried with sodium sulfate and concentrated under reduced pressure to give 5-acetamino-4-fluoro-2-methyl-benzenethiol as a crude intermediate (270 g, 72%).

Crude 5-acetamino-4-fluoro-2-methyl-benzenethiol (280 g, 1.41 mol) was added to a 5% (w/w) solution of potassium hydroxide (250 g, 4.46 mol) in water and the mixture was refluxed for 5 hours. The resulting solution was adjusted to pH 7 with dilute hydrochloric acid and was then extracted with ethyl acetate. The organic phase was dried with sodium sulfate and concentrated under reduced pressure to give 5-amino-4-fluoro-2-methyl-benzenethiol as a crude intermediate (160 g, 88%).

$^1$H NMR (400 MHz, CDCl$_3$): δ=7.18 (d, 1H, J=1.6 Hz), 6.66-6.74 (m, 2H), 3.2-3.67 (m, 2H), 3.03-3.14 (m, 1H), 2.10-2.15 (m, 3H).

To a solution of potassium hydroxide (78.5 g, 1.4 mol), sodium hydroxymethylsulfinate (Rongalite®, 74.4 g, 0.63 mol) and the crude 5-amino-4-fluoro-2-methyl-benzenethiol (110 g, 0.7 mol) in 380 mL of DMF was added dropwise 2,2,2-trifluoroethyl iodide (147.1 g, 0.704 mol). The reaction mixture was stirred for 2 hours at room temperature, poured into water and then extracted with ethyl acetate. The organic phase was dried with sodium sulfate and concentrated under reduced pressure to yield the title compound (176 g, 99%).

$^1$H NMR (400 MHz, CDCl$_3$): δ=6.84-6.89 (m, 1H), 6.7-6.78 (m 1H), 3.4-3.7 (m, 3H), 3.14-3.25 (m, 2H), 2.22-2.26 (m, 3H).

1.3 N-(2-Nitro-benzoyl)-3-(2,2,2-trifluoroethylsulfanyl)-4-methyl-6-fluoro-anilide 3-(2,2,2-Trifluoroethylsufanyl)-4-methyl-6-fluoroaniline (4.0 g, 16.7 mmol) was dissolved in 100 mL DMF. 2-Nitrobenzoic acid (2.79 g, 16.7 mmol) and triethylamine (2.02 g, 20 mmol) were added to the solution. After cooling to a temperature of 0° C. HATU (7.62 g, 20 mmol) was added in one portion and the resulting mixture was stirred overnight at room temperature. Water was added to the reaction mixture, which was then extracted with ethyl acetate. The organic phase was dried with sodium sulfate and the crude product was purified by column chromatography on silica gel to give the title compound (5 g, 76.9%) as a yellow solid.

$^1$H NMR (400 MHz, CDCl$_3$): δ=8.6 (d, 1H, J=7.6 Hz), 8.2 (d, 1H, J=8 Hz), 7.73-7.76 (m, 1H), 7.61-7.67 (m, 3H), 7.0 (s, 1H), 3.39-3.46 (m, 2H), 2.45 (s, 3H).

1.4 2-(2,2,2-trifluoroethylsulfanyl)-4-(4-oxoquinazolin-3-yl)-5-fluoro-toluol To a suspension of N-(2-nitro-benzoyl)-3-(2,2,2-trifluoroethylsulfanyl)-4-methyl-6-fluoroanilide (2.3 g, 5.9 mmol) in 230 mL ethanol was added Raney nickel (0.8 g) and the stirred mixture was hydrogenated at ambient pressure overnight at room temperature. The solid was filtered off and the filtrate was evaporated to give the intermediate N-(2-amino-benzoyl)-3-(2,2,2-trifluoroethylsulfanyl)-4-methyl-6-fluoro-anilide (2 g, 95%) as a white solid.

$^1$H NMR (400 MHz, DMSO-d$_6$): δ=9.79 (s, 1H), 7.75-7.71 (m, 2H), 7.16-7.24 (m, 2H), 6.72 (d, 1H, J=8.4 Hz), 6.55 (t, 1H, J=7.4 Hz), 6.44 (s, 2H), 3.79-3.87 (m, 2H), 2.38 (s, 3H).

A mixture of the amine N-(2-amino-benzoyl)-3-(2,2,2-trifluoroethylsulfanyl)-4-methyl-6-fluoro-anilide (2.3 g, 6.4 mmol), concentrated sulfuric acid (2 mL) and 1,1,1-triethoxymethane (100 mL) were heated to 140° C. and stirred for 5 hours at this temperature. The mixture was cooled to room temperature, excess of solvent was removed under reduced pressure and the crude product was purified by column chromatography on silica gel to yield the title compound (1.4 g, 59%) as an off-white solid.

$^1$H NMR (400 MHz, CDCl$_3$): δ=8.28-8.31 (m, 1H), 7.94 (s, 1H), 7.71-7.78 (m, 2H), 7.48-7.53 (m, 2H), 7.13-7.16 (m, 1H), 3.27-3.34 (m, 2H), 2.50 (s, 3H).

Melting point: 145-147° C.

Example 2

Compound I-2

2-(2,2,2-trifluoroethylsufinyl)-4-(4-oxo-quinazolin-3-yl)-5-fluoro-toluol (Compound of formula I, wherein k is 0, n is 1, R$^1$ is F$_3$C—CH$_2$, R$^2$ is F, R$^3$ is H, Y$^1$ is CH, Y$^2$ is C—CH$_3$ and X is O)

2-(2,2,2-Trifluoroethylsulfanyl)-4-(4-oxo-quinazolin-3-yl)-5-fluoro-toluol (0.80 g, 1.96 mmol) was dissolved in 20 mL chloroform and meta-chloroperoxybenzoic acid (0.466 g, 2.29 mmol, 85% of purity) was added under ice-cooling. The reaction mixture was stirred for 1 hour at ice bath temperature. The solution was washed successively with an aqueous solution of sodiumthiosulfate and an aqueous solution of sodiumhydrogencarbonate, and dried with sodium sulfate. After removing excess solvent under reduced pressure the crude product was purified by column chromatography on silica gel to give the title compound (0.32 g, 42.9%) as an off-white solid.

$^1$H NMR (400 MHz, CDCl$_3$): δ=8.34-8.36 (m, 1H), 8.08 (d, 1H, J=7.2 Hz), 8.02 (s, 1H), 7.48-7.53 (m, 2H), 7.79-7.87 (m, 2H), 7.56-7.6 (m, 1H), 7.24-7.26 (m, 1H), 3.47-3.55 (m, 2H), 2.49 (s, 3H).

Melting point: 184-186° C.

Example 3

Compound I-3

2-(2,2,2-trifluoroethylsufanyl)-4-(2-methyl-4-oxo-quinazolin-3-yl)-5-fluoro-toluol (Compound of formula I, wherein k is 0, n is 0, R$^1$ is F$_3$C—CH$_2$, R$^2$ is F, R$^3$ is CH$_3$, Y$^1$ is CH, Y$^2$ is C—CH$_3$ and X is O)

A mixture of the amine N-(2-amino-benzoyl)-3-(2,2,2-trifluoroethylsulfanyl)-4-methyl-6-fluoro-anilide (1.45 g, 4 mmol, as prepared according to the synthesis described in Example 1), concentrated sulfuric (2 mL) acid and 1,1,1-triethoxyethane (100 mL) were heated to 140° C. and stirred for 5 hours at this temperature. The mixture was cooled to room temperature, excess of solvent was removed under reduced pressure and the crude product was purified by column chromatography on silica gel to yield the title compound (1.3 g, 85%) as an off-white solid.

$^1$H NMR (400 MHz, CDCl$_3$): δ=8.23~8.26 (m, 1H), 7.74~7.78, (m, 2H), 7.67 (d, 1H, J=8 Hz), 7.44~7.49 (m, 2H), 7.19 (d, 1H, J=10 Hz), 3.29~3.39 (m, 2H), 2.55 (s, 3H), 2.26 (s, 3H)

Melting point: 95-96° C.

Example 4

Compound I-4

2-(2,2,2-trifluoroethylsufinyl)-4-(2-methyl-4-oxo-quinazolin-3-yl)-5-fluoro-toluol (Compound of formula I, wherein k is 0, n is 1, R$^1$ is F$_3$C—CH$_2$, R$^2$ is F, R$^3$ is CH$_3$, Y$^1$ is CH, Y$^2$ is C—CH$_3$ and X is O)

2-(2,2,2-Trifluoroethylsulfanyl)-4-(2-methyl-4-oxo-quinazolin-3-yl)-5-fluoro-toluol (0.50 g, 1.31 mmol) was dissolved in 20 mL chloroform and meta-chloroperoxybenzoic acid (0.265 g, 1.53 mmol, 85% of purity) was added under ice-cooling. The reaction mixture was stirred for 1 hour at ice bath temperature. The solution was washed successively with an aqueous solution of sodiumthiosulfate and an aqueous solution of sodiumhydrogencarbonate, and dried with sodium sulfate. After removing excess solvent under reduced pressure the crude product was purified by column chromatography on silica gel to give the title compound (0.3 g, 57.5%) as an off-yellow solid.

$^1$H NMR (400 MHz, CDCl$_3$): δ=8.23~8.26 (m, 1H), 7.93~7.97 (m, 1H), 7.78~7.82 (m, 2H), 7.71 (d, 1H, J=8.4 Hz), 7.49~7.53 (m, 1H), 7.24~7.26 (m, 1H), 3.47~3.55 (m, 2H), 2.55 (s, 3H), 2.29~2.31 (m, 3H).

Melting point: 188-190° C.

Example 6

Compound I-6

3-[2-(2,2,2-Trifluoro-ethylsulfanyl)-pyrimidin-4-yl]-3H-quinazolin-4-one 6.1 2-(2,2,2-Trifluoro-ethylsulfanyl)-3H-pyrimidin-4-one To solution of 2-thioxo-2,3-dihydro-1H-pyrimidin-4-one (14 g, 0.109 mol) in dimethylformamide (300 mL) was added NaH (13.1 g, 0.327 mol). When the addition was complete, the solution was stirred at 40° C. for 1.5 hours, and 2,2,2-trifluoroethyliodide (27.4 g, 0.131 mol) was added to the solution. The reaction was stirred at 40° C. for 3 hours. The solvent was removed and the residue was poured into water, the mixture was adjusted to pH 3-4 with dilute HCl and extracted with ethyl acetate, the organic layer was dried over Na$_2$SO$_4$ and concentrated under reduced pressure to give 2-(2,2,2-trifluoroethylsulfanyl)-3H-pyrimidin-4-one (26 g, crude) as solid.

$^1$H NMR: (400 MHz, CDCl$_3$): δ 7.93 (d, 1H, J=6.8 Hz), 6.32 (d, 1H, J=6.8 Hz), 4.07-4.0 (m, 2H).

6.2 4-Chloro-2-(2,2,2-trifluoro-ethylsulfanyl)-pyrimidine

The solution of 2-(2,2,2-trifluoro-ethylsulfanyl)-3H-pyrimidin-4-one (25 g, crude) in POCl$_3$ (250 mL) was stirred and refluxed for 5 hours. After most POCl$_3$ was removed, the residue was dropped into ice and the pH was adjusted to 8-9, extracted with ethyl acetate, dried over MgSO$_4$ and the crude material was purified by column chromatography on silica gel to give 4-chloro-2-(2,2,2-trifluoro-ethylsulfanyl)-pyrimidine (14.6 g, 58.8%) as an oil.

¹H NMR: (400 MHz, CDCl₃): δ 8.45~8.43 (m, 1H), 7.12~7.10 (m, 1H), 4.02~3.95 (m, 2H).

6.3 2-(2,2,2-Trifluoro-ethylsulfanyl)-pyrimidin-4-yl amine

To solution of 4-chloro-2-(2,2,2-trifluoro-ethylsulfanyl)-pyrimidine (22 g, 0.096 mol) in 350 mL of CH₃CN was added NH₄OH (400 mL). The mixture was stirred for 24 hours at 90° C. in a sealed tube. The mixture was then cooled to room temperature and the solvent was concentrated in vacuo, the residue was extracted with ethyl acetate, dried over MgSO₄ and the crude was purified by column chromatography on silica gel to give 2-(2,2,2-trifluoro-ethylsulfanyl)-pyrimidin-4-ylamine (14.3 g, 71.3%) as a white solid.

¹H NMR: (400 MHz, CDCl₃): δ 8.08 (d, 1H, J=6 Hz), 6.20-6.18 (m, 1H), 4.94 (s, 2H), 3.99~3.91 (m, 2H).

6.4 2-Nitro-N-[2-(2,2,2-trifluoro-ethylsulfanyl)-pyrimidin-4-yl]-benzamide

A solution of 2-nitrobenzoyl chloride (1.85 g, 10 mmol) in CH₂Cl₂ (10 mL) was slowly added to a solution of 2-(2,2,2-trifluoro-ethylsulfanyl)-pyrimidin-4-ylamine (2.1 g, 10 mmol) and triethylamine (2 g, 20 mmol) in CH₂Cl₂ (80 mL) between 0 and max 7° C. The mixture was stirred overnight at room temperature and then poured into ice-water. The phases were separated and the organic part was dried with Na₂SO₄, filtered and concentrated in vacuo to provide a viscous oil. The crude product was purified by prep-HPLC (1.5 g, 41.8%).

¹H NMR (400 MHz, CDCl₃): δ 3.058-3.087 (m, 2H), 7.558-7.581 (m, 1H), 7:635-7.659 (m, 1H), 7.702-7.723 (m, 1H), 7.939-7.954 (m, 1H), 8.110-8.133 (m, 1H), 8.466-8.480 (m, 1H).

6.5 2-Amino-N-[2-(2,2,2-trifluoro-ethylsulfanyl)-pyrimidin-4-yl]-benzamide

To the solution of compound 2 (1.5 g, 4.2 mmol) in acetic acid (14.4 ml) and tetrahydrofuran (21 ml) was added HCl (0.69 ml), and then Zn (2.745 g) at 0° C. The mixture was stirred at room temperature for 2 hrs. NaHCO₃ solution was added to adjust the pH to 8. The mixture was extracted with ethyl acetate. The organic layer was dried, concentrated to give the crude product (1.5 g).

6.6 3-[2-(2,2,2-Trifluoro-ethylsulfanyl)-pyrimidin-4-yl]-3H-quinazolin-4-one Compound 2 (1.5 g, 4.2 mmol), 2 mL concentrated sulfuric acid and 1,1,1-triethoxymethane (100 mL) were heated to 140° C. and stirred for 5 hours. The mixture was cooled to room temperature, the excess of solvent was distilled and the crude was purified by column chromatography on silica gel to give 3-[2-(2,2,2-trifluoro-ethylsulfanyl)-pyrimidin-4-yl]-3H-quinazolin-4-one (500 mg, 35%) as an off-white solid.

¹H NMR (400 MHz, CDCl₃): δ 3.956-4.031 (m, 2H), 7.568-7.606 (m, 1H), 7.777-7.797 (m, 1H), 7.828-7.869 (m, 1H), 7.931-7.948 (m, 1H), 8.707-8.723 (m, 1H), 8.823 (s, 1H).

Example 11

Compound I-11

3-[2-(2,2,2-Trifluoro-ethylsulfinyl)-pyrimidin-4-yl]-3H-quinazolin-4-one

3-[2-(2,2,2-Trifluoro-ethylsulfanyl)-pyrimidin-4-yl]-3H-quinazolin-4-one (1.1 g, 3.25 mmol) was dissolved in 20 mL chloroform, and m-chloroperoxybenzoic acid (m-CPBA) (0.7 g, 3.57 mmol, 85% of purity) was added at room temperature. The reaction mixture was stirred for 3 hours at room temperature. Washing with sodium-thiosulfate solution and sodium-hydrogencarbonate, drying with Na₂SO₄ and the crude product was purified by prep-TLC and then prep-HPLC to give 3-[2-(2,2,2-trifluoro-ethylsulfinyl)pyrimidin-4-yl]-3H-quinazolin-4-one (0.35 g, 30.5%) as an off-white solid.

¹H NMR (400 MHz, CDCl₃): δ 3.77-3.84 (m, 1H), 4.06-4.12 (m, 1H), 7.58-7.62 (m, 1H), 7.79-7.89 (m, 2H), 8.37-8.39 (m, 1H), 8.43-8.49 (m, 1H), 8.98 (s, 1H), 9.04-9.06 (m, 1H).

The procedure described in the synthesis examples 1 to 4 above were used to prepare further compounds I-A, namely compounds I-5, I-7 to I-10 and I-12 to I-35, with X being oxygen by appropriate modification of the starting compounds. The compounds thus obtained are listed in the table C below, and their physical data are listed in table D below.

TABLE C (I-A)

| Compound | (R)ₖ | R³ | R² | R⁵ | R¹ | n |
|---|---|---|---|---|---|---|
| I-5 | k = 0 | H | F | CH₃ | CF₃—CH₂— | 2 |
| I-7 | k = 0 | H | F | CH₃ | n-propyl | 0 |
| I-8 | k = 0 | H | F | CH₃ | n-propyl | 1 |
| I-9 | 8-CH₃ | H | F | CH₃ | CF₃—CH₂— | 0 |
| I-10 | 8-CH₃ | H | F | CH₃ | CF₃—CH₂— | 1 |
| I-12 | 8-Cl | H | F | CH₃ | CF₃—CH₂— | 0 |
| I-13 | 8-Cl | H | F | CH₃ | CF₃—CH₂— | 1 |
| I-14 | k = 0 | H | F | CH₃ | 3,4,4-trifluoro-3-buten-1-yl | 0 |
| I-15 | k = 0 | H | F | CH₃ | 3,4,4-trifluoro-3-buten-1-yl | 1 |
| I-16 | k = 0 | H | H | CH₃ | CF₃—CH₂— | 0 |
| I-17 | k = 0 | H | H | CH₃ | CF₃—CH₂— | 1 |
| I-18 | k = 0 | H | F | CH₃ | cyclopropylmethyl | 0 |
| I-19 | k = 0 | H | F | CH₃ | cyclopropylmethyl | 1 |
| I-20 | 6-Cl | H | F | CH₃ | CF₃—CH₂— | 0 |
| I-21 | 6-Cl | H | F | CH₃ | CF₃—CH₂— | 1 |
| I-22 | 7-CH₃ | H | F | CH₃ | CF₃—CH₂— | 0 |
| I-23 | 7-CH₃ | H | F | CH₃ | CF₃—CH₂— | 1 |
| I-24 | 7-Cl | H | F | CH₃ | CF₃—CH₂— | 0 |
| I-25 | 7-Cl | H | F | CH₃ | CF₃—CH₂— | 1 |
| I-26 | 6-OCH₃ | H | F | CH₃ | CF₃—CH₂— | 0 |
| I-27 | 6-OCH₃ | H | F | CH₃ | CF₃—CH₂— | 1 |
| I-28 | 5-CH₃ | H | F | CH₃ | CF₃—CH₂— | 0 |
| I-29 | 5-CH₃ | H | F | CH₃ | CF₃—CH₂— | 1 |
| I-30 | 6-CH₃ | H | F | CH₃ | CF₃—CH₂— | 0 |
| I-31 | 6-CH₃ | H | F | CH₃ | CF₃—CH₂— | 1 |
| I-32 | 5-Cl | H | F | CH₃ | CF₃—CH₂— | 0 |
| I-33 | 5-Cl | H | F | CH₃ | CF₃—CH₂— | 1 |
| I-34 | k = 0 | H | CH₃ | CH₃ | CF₃—CH₂— | 0 |
| I-35 | k = 0 | H | CH₃ | CH₃ | CF₃—CH₂— | 1 |

TABLE D

| Compound | Physico-chemical data: $^1$H-NMR (400 MHz) δ or r.t. [min]/M$^+$ |
| --- | --- |
| I-5 | 3.13 min/400.05 |
| I-7 | CDCl$_3$: 8.39~8.36 (m, 1H), 8.01 (s, 1H), 7.84~7.77 (m, 2H), 7.58~7.54 (m, 1H), 7.28~7.25 (m, 1H), 7.17 (d, 1H, J = 10.4 Hz), 2.88~2.84 (m, 2H), 2.45 (s, 3H), 1.74~1.65 (m, 2H), 1.06~1.04 (m, 3H) |
| I-8 | CDCl$_3$: 8.37~8.35 (m, 1H), 8.01 (s, 1H), 8.01 (s, 1H), 7.98 (d, 1H, J = 7.0 Hz), 7.85~7.78 (m, 2H), 7.59~7.55 (m, 1H), 7.18 (d, 1H, J = 10 Hz), 2.86~2.72 (m, 2H), 2.46 (s, 3H), 1.94~1.73 (m, 2H), 1.25 (s, 3H) |
| I-9 | CD$_3$OD: 8.19 (s, 1H), 8.13~8.11 (m, 1H), 7.78 (d, 1H, J = 7.2 Hz), 7.33 (d, 1H, J = 10.8 Hz), 3.73~3.66 (m, 2H), 2.64 (s, 3H), 2.56 (s, 3H) |
| I-10 | CDCl$_3$: 8.13 (d, 1H, J = 8 Hz), 8.01 (d, 1H, J = 7.2 Hz), 7.94 (s, 1H), 7.62 (d, 1H, J = 7.2 Hz), 7.41~7.31 (m, 1H), 7.19~7.17 (m, 1H), 3.48~3.40 (m, 2H), 2.6 (s, 3H), 2.42 (s, 3H) |
| I-12 | CD$_3$OD: 8.29 (s, 1H), 8.24~8.21 (m, 1H), 7.99~7.97 (m, 1H), 7.80 (d, 1H, J = 7.2 Hz), 7.58~7.54 (m, 1H), 7.35~7.32 (m, 1H), 3.73~3.66 (m, 2H), 2.56 (s, 3H) |
| I-13 | CD$_3$OD: 8.36 (s, 1H), 8.25~8.23 (m, 1H), 8.12 (d, 1H, J = 7.2 Hz), 8.01~7.99 (m, 1H), 7.60~7.55 (m, 1H), 7.46~7.45 (m, 1H), 4.09~3.84 (m, 2H), 2.53 (s, 3H) |
| I-14 | CDCl$_3$: 8.31~8.29 (m, 1H), 7.93 (s, 1H), 7.78~7.70 (m, 2H), 7.52~7.48 (m, 1H), 7.30~7.28 (d, 1H, J = 7.2 Hz), 7.12~7.1 (d, 1H, J = 10 Hz), 3.01~2.98 (m, 2H), 2.61~2.50 (m, 2H), 2.41 (s, 3H) |
| I-15 | CDCl$_3$: 8.36 (t, 1H, J = 0.8 Hz), 8.02 (d, 1H, J = 0.8 Hz), 8.00 (d, 1H, J = 7.2 Hz), 7.61~7.56 (m, 1H), 7.23 (d, 1H, J = 9.6 Hz), 3.15~3.11 (m, 1H), 3.09~2.87 (m, 2H), 2.87~2.68 (m, 1H), 2.47 (s, 3H) |
| I-16 | DMSO-d$_6$: 8.32 (s, 1H), 8.21 (d, 1H, J = 8 Hz), 7.90-7.88 (m, 1H), 7.46-7.23 (m, 2H), 7.63-7.61 (m, 1H), 7.45-7.43 (m, 1H), 7.37 (dd, 1H, J = 1 Hz, 8 Hz), 4.08-4.06 (m, 2H), 2.42 (s, 3H) |
| I-17 | DMSO-d$_6$: 8.41 (s, 1H), 8.22 (d, J = 8 Hz), 7.91 (dd, 1H, J = 1.6 Hz, 7.6 Hz), 7.89 (d, 1H, J = 7.6 Hz), 7.78-7.70 (m, 2H), 7.64-7.55 (m, 1H), 7.26-7.04 (m, 2H), 2.32 (s, 3H) |
| I-18 | CDCl$_3$: 8.14 (d, 1H, J = 9.2 Hz), 7.79 (s, 1H), 7.59~7.54 (m, 2H), 7.35~7.13 (m, 1H), 7.08 (d, 1H, J = 7.2 Hz), 6.91 (d, 1H, J = 12.4 Hz), 2.58 (d, 1H, J = 6.8 Hz), 2.24 (s, 3H), 0.82~0.80 (m, 1H), 0.39~0.34 (m, 2H), 0.04~0.03 (m, 2H) |
| I-19 | CDCl$_3$: 8.36~8.34 (m, 1H), 8.02~8.00 (m, 2H), 7.83~7.78 (m, 2H), 7.58 (t, 1H, J = 5.6 Hz), 7.17 (d, 1H, J = 10.4 Hz), 2.81~2.75 (m, 2H), 2.46 (s, 3H), 1.10~1.086 (m, 1H), 0.71~0.66 (m, 2H), 0.31~0.28 (m, 2H) |
| I-20 | CDCl$_3$: 8.25 (d, 1H, J = 2.4 Hz), 7.910 (s, 1H), 7.707~7.647 (m, 2H), 7.51 (d, 1H, J = 7.2 Hz), 7.16 (t, 1H, J = 11.2 Hz), 3.341~3.269 (m, 2H), 2.500 (s, 3H) |
| I-21 | CDCl$_3$: 8.24 (d, 1H, J = 2.8 Hz), 8.010~7.923 (m, 1H), 7.921 (s, 1H), 7.724~7.663 (m, 2H), 7.206~7.181 (m, 1H), 3.478~3.404 (m, 2H), 2.425 (s, 3H) |
| I-22 | CD$_3$OD: 8.25 (d, 1H, J = 8 Hz), 7.97 (d, 1H, J = 0.8 Hz), 7.61~7.58 (m, 2H), 7.41~7.39 (m, 1H), 7.23~7.21 (m, 1H) 3.43~3.36 (m, 2H), 2.58 (s, 3H), 2.56 (s, 3H) |
| I-23 | CDCl$_3$: 8.24 (d, 1H, J = 8 Hz), 8.09 (d, 1H, J = 7.2 Hz), 7.99 (s, 1H), 7.59 (s, 1H), 7.42~7.39 (m, 1H), 7.26 (d, 1H, J = 10.4 Hz), 3.57~3.48 (m, 2H), 2.56 (s, 3H), 2.50 (s, 3H) |
| I-24 | CDCl$_3$: 8.22 (d, 1H, J = 7.6 Hz), 7.93 (s, 1H), 7.71 (d, 1H, J = 2 Hz), 7.51 (d, 1H, J = 7.2 Hz), 7.46~7.44 (m, 1H), 7.15 (d, 1H, J = 10 Hz), 3.34~3.27 (m, 2H), 2.5 (s, 3H) |
| I-25 | CDCl$_3$: 8.33 (s, 1H), 8.27 (d, 1H, J = 8.8 Hz), 8.10 (d, 1H, J = 7.6 Hz), 7.80 (d, 1H, J = 2 Hz), 7.64~7.62 (m, 1H), 7.45 (d, 1H, J = 10.4 Hz), 4.02~3.89 (m, 2H), 2.53 (s, 3H) |
| I-26 | CDCl$_3$: 7.92 (d, 1H, J = 1.2 Hz), 7.92~7.72 (m, 2H), 7.60 (d, 1H, J = 7.2 Hz), 7.44~7.41 (m, 1H), 7.28 (s, 1H), 7.23 (d, 1H, J = 10.4 Hz), 3.95 (s, 3H), 3.43~3.36 (m, 2H), 2.58 (s, 3H) |
| I-27 | CDCl$_3$: 8.10 (d, 1H, J = 7.2 Hz), 7.93 (s, 1H), 7.75~7.07 (m, 2H), 7.45~7.42 (m, 1H), 7.27 (d, 1H, J = 8.8 Hz), 3.95 (s, 3H), 3.57~3.50 (m, 2H), 2.51 (s, 3H) |
| I-28 | CDCl$_3$: 7.95 (s, 1H), 7.67~7.61 (m, 2H), 7.57 (d, 1H, J = 7.2 Hz), 7.32 (d, 1H, J = 7.2 Hz), 7.20 (d, 1H, J = 10.4 Hz), 3.41~3.34 (m, 2H), 2.87 (s, 3H), 2.56 (s, 3H) |
| I-29 | CDCl$_3$: 8.07~8.05 (m, 1H), 7.95 (d, 1H, J = 0.8 Hz), 7.69~7.61 (m, 2H), 7.34~7.32 (m, 1H), 7.25~7.23 (m, 1H), 3.56~3.45 (m, 2H), 2.87 (s, 3H) 2.48 (s, 3H) |
| I-30 | CDCl$_3$: 8.14 (s, 1H), 7.94 (s, 1H), 7.69~7.62 (m, 2H), 7.58 (d, 1H, J = 7.6 Hz), 7.21 (d, 1H, J = 10 Hz), 3.41~3.34 (m, 2H), 2.56 (s, 3H), 2.52 (s, 3H) |
| I-31 | CDCl$_3$: 8.25 (s, 1H), 8.14 (d, 2H, J = 7.2 Hz), 7.74-7.76 (m, 2H), 7.70-7.68 (m, 1H), 7.46-7.43 (m, 1H), 4.06-3.88 (m, 2H), 2.53 (s, 6H) |
| I-32 | CDCl$_3$: 7.99 (d, 1H, J = 0.8 Hz), 7.67~7.66 (m, 2H), 7.61~7.56 (m, 2H), 7.22 (d, 1H, J = 10 Hz), 3.43~3.35 (m, 2H), 2.58 (s, 3H) |
| I-33 | CDCl$_3$: 8.07 (d, 1H, J = 7.2 Hz), 7.98 (d, 1H, J = 0.8 Hz), 7.70~7.69 (m, 2H), 7.59~7.56 (m, 1H), 7.25~7.23 (m, 1H), 2.49 (s, 3H) |

TABLE D-continued

| Compound | Physico-chemical data: $^1$H-NMR (400 MHz) δ or r.t. [min]/M$^+$ |
|---|---|
| I-34 | 3.62 min/365.05 |
| I-35 | 2.75 min/380.90 | r.t. = retention time (HPLC); acetic acid served as mobile phase; flow rate: 1.8 mL/min and injection volume: 2 μl
M$^+$ = molecular mass of the detected cationic species

II. EVALUATION OF PESTICIDAL ACTIVITY

II.1. Diamond Back Moth (*Plutella xylostella*)

II.1.a)

The active compound was dissolved at the desired concentration in a mixture of 1:1 (vol:vol) acetone:water. The test solution was prepared at the day of use.

Ten, third-istar larvae are sprayed with 1 ml test solution and introduced to untreated leaves held in a petri dish that was lined with moist filter paper. Mortality was recorded 24, 72 and 120 hours after treatment.

In this test, the compound of Example 3 (compound I-3) showed 100% mortality at 500 ppm in comparison with untreated controls.

II.1.b)

The active compounds were formulated in 50:50 acetone:water and 0.1% (vol/vol) Alkamuls EL 620 surfactant. A 6 cm leaf disk of cabbage leaves was dipped in the test solution for 3 seconds and allowed to air dry in a Petri plate lined with moist filter paper. The leaf disk was inoculated with 10 third instar larvae and kept at 25-27° C. and 50-60% humidity for 3 days. Mortality was assessed after 72 h of treatment.

In this test, the compounds I-3 and I-5 at 300 ppm showed a mortality of at least 50% in comparison with untreated controls.

II.2. Silverleaf Whitefly (*Bemisia argentifolli*, adult)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v). Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and 10 to 12 whitefly adults (approximately 3-5 days old) were introduced. The insects were collected using an aspirator and 0.6 cm, nontoxic Tygon® tubing (R-3603) connected to a barrier pipette tip. The tip, containing the collected insects, was then gently inserted into the soil containing the treated plant, allowing insects to crawl out of the tip to reach the foliage for feeding. Cups were covered with a reusable screened lid (150-micron mesh polyester screen PeCap from Tetko, Inc.). Test plants were maintained in a growth room at 25° C. and 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, compounds I-24 and I-16 at 300 ppm showed a mortality of at least 50% in comparison with untreated controls.

II.3. Activity Against Cowpea Aphid (*Aphis craccivora*)

The active compounds were formulated in 50:50 (vol:vol) acetone:water. The test solution was prepared at the day of use.

Potted cowpea plants colonized with 100-150 aphids of various stages were sprayed after the pest population had been recorded. Population reduction was assessed after 72 hours.

In this test, the compound I-6 at 300 ppm showed a mortality of at least 50% in comparison with untreated controls.

II.4. Rice Plant Hopper (*Nilaparvata ugens*)

Rice seedlings were cleaned and washed 24 hours before spraying. The active compounds were formulated in 50:50 acetone:water and 0.1% vol/vol surfactant (EL 620) was added. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours. In this test, compound I-15 at a concentration of the test solution of 300 ppm showed a mortality of at least 50% in comparison with untreated controls.

II.5. Rice Green Leafhopper (*Nephotettix virescens*)

Rice seedlings were cleaned and washed 24 hours before spraying. The active compounds were formulated in 50:50 acetone:water, and 0.1% vol/vol surfactant (EL 620) was added. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours.

In this test, compounds I-15 at a concentration of the test solution of 300 ppm showed a mortality of at least 50% in comparison with untreated controls.

II.6. 2-Spotted Spider Mite (*Tetranychus urticae*)

The active compounds were formulated in 50:50 (vol:vol) acetone:water and 100 ppm Kinetica™ surfactant.

Sieva lima bean plants with primary leaves expanded to 7-12 cm were infested by placing on each a small piece from an infested leaf (with about 100 mites) taken from the main colony. This was done at about 2 hours before treatment to allow the mites to move over to the test plant to lay eggs. The piece of leaf used to transfer the mites was removed. The newly-infested plants were dipped in the test solution and allowed to dry. The test plants were kept under fluorescent light (24 hour photoperiod) at about 25° C. and about 20-40% relative humidity. After 5 days, one leaf was removed and mortality counts were made.

In this test, compounds I-1, I-2, I-18, I-19, I-20, I-21, I-24, I-25, I-26, I-34, I-35 at a concentration of the test solution of 300 ppm showed a mortality of at least 50% in comparison with untreated controls.

II.7. Kanzawa Spider Mite (*Tetranychus kanzawai*)

II.7.a)

The active compounds were dissolved at the desired concentration in a mixture of 1:1 (vol:vol) acetone:water. The test solutions were prepared at the day of use.

Potted cotton plants colonized with approximately 50 mites of various stages were sprayed after the pest population had been recorded. Population reductions (or increases) after 24, 72 and 120 hours were assessed.

In this test, the compounds of Examples 1 and 2, i.e. compounds I-1 and I-2, showed 100% mortality at 300 ppm in comparison with untreated controls.

II.7.b)

Potted cotton plants colonized with approximately 50 mites of various stages will be sprayed after the pest population has been recorded. Assess population reduction (or increase) after 72 hours.

In this test, compounds I-1, I-2 and I-15 at a concentration of the test solution of 300 ppm showed a mortality of at least 50% in comparison with untreated controls.

The invention claimed is:

1. A compound of the Formula (I):

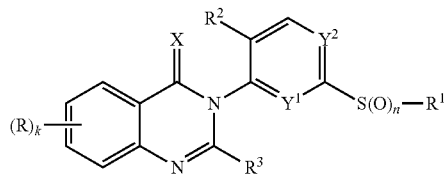

(I)

wherein
k is 0, 1, 2, 3 or 4;
n is 0, 1 or 2;
X is O, S or N—$R^4$;
$Y^1$ is N or CH;
$Y^2$ is N or C—$R^5$;
R is selected from the group consisting of halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, for k being 2, 3 or 4 it being possible that R is identical or different;
$R^1$ is $C_1$-$C_{10}$-alkyl, $C_1$-$C_{10}$-haloalkyl, $C_2$-$C_{10}$-alkenyl, $C_2$-$C_{10}$-haloalkenyl, $C_3$-$C_{12}$-cycloalkyl-$C_1$-$C_4$-alkyl, where the cyclalkyl radical and the cycloalkenyl radical in the last four mentioned radicals are unsubstituted, partially or fully halogenated and/or carry 1, 2, 3, 4, or 5 $C_1$-$C_4$-alkyl radicals;
$R^2$ is hydrogen, halogen, CN, $C_1$-$C_4$-alkyl or $C_1$-$C_4$-haloalkyl;
$R^3$ is hydrogen, halogen, CN, $C_1$-$C_4$-alkyl, $C_1$-$C_4$-haloalkyl, $C_1$-$C_4$-alkoxy, $C_1$-$C_4$-haloalkoxy;
$R^4$ is selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_4$-alkyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_3$-$C_6$-cycloalkyl, $C_5$-$C_6$-cycloalkenyl, $C_3$-$C_6$-cycloalkyl-$C_1$-$C_4$-alkyl, $C_5$-$C_6$-cycloalkenyl-$C_1$-$C_4$-alkyl, $C_3$-$C_6$-cycloalkoxy, $C_5$-$C_6$-cycloalkenoxy, $C_3$-$C_6$-cycloalkyl-$C_1$-$C_4$-alkoxy, and $C_5$-$C_6$-cycloalkenyl-$C_1$-$C_4$-alkoxy, where the cycloalkyl radical and the cycloalkenyl radical in the last eight mentioned radicals are unsubstituted, partially or fully halogenated and/or carry 1, 2, 3, 4, or 5 $C_1$-$C_4$-alkyl radicals, phenyl, phenyl-$C_1$-$C_4$-alkyl, phenyloxy and phenyl-$C_1$-$C_4$-alkoxy, wherein the phenyl ring of phenyl, phenyl-$C_1$-$C_4$-alkyl, phenyl-$C_1$-$C_4$-alkoxy and phenoxy is unsubstituted or substituted by 1, 2, 3, 4 or 5 substituents selected from halogen, $C_1$-$C_4$-alkyl, $C_1$-$C_4$-haloalkyl, $C_1$-$C_4$-alkoxy and $C_1$-$C_4$-haloalkoxy; and
$R^5$ is hydrogen, halogen, CN, $C_1$-$C_4$-alkyl or $C_1$-$C_4$-haloalkyl;
or an agriculturally acceptable salt thereof.

2. The compound according to claim 1, wherein $R^1$ is $C_1$-$C_4$-alkyl, fluorinated $C_1$-$C_4$-alkyl, $C_2$-$C_4$-alkenyl, fluorinated $C_2$-$C_4$-alkenyl, or cyclopropylmethyl.

3. The compound according to claim 2, wherein $R^1$ is 2,2,2-trifluoroethyl.

4. The compound according to claim 1, wherein $R^2$ is hydrogen, fluorine, chlorine or methyl.

5. The compound according to claim 4, wherein $R^2$ is hydrogen or fluorine.

6. The compound according to claim 5, wherein $R^3$ is hydrogen.

7. The compound according to claim 1, wherein k is 0.

8. The compound according to claim 1, wherein k is 1, 2 or 3 and wherein R is selected from fluorine, chlorine, CN, $NO_2$, methyl and methoxy, for k being 2 or 3 it being possible that R is identical or different.

9. The compound according to claim 1, wherein X is O.

10. The compound according to claim 1, wherein $Y^1$ is CH and $Y^2$ is C—$R^5$.

11. The compound according to claim 10, wherein $R^5$ is chlorine, methyl, difluoromethyl, trifluoromethyl or cyano.

12. The compound according to claim 1, wherein $Y^1$ and $Y^2$ are N.

13. The compound according to claim 1, wherein n is 0.

14. The compound according to claim 1, wherein n is 1.

15. The compound according to claim 1, wherein n is 2.

16. An agricultural composition comprising at least one compound of claim 1, and at least one liquid or solid carrier.

* * * * *